(12) United States Patent
Jung et al.

(10) Patent No.: US 8,466,180 B2
(45) Date of Patent: Jun. 18, 2013

(54) INSECTICIDAL COMPOUNDS

(75) Inventors: Pierre Joseph Marcel Jung, Huningue (FR); Stephan Trah, Freiburg (DE); Christopher Richard Ayles Godfrey, Olsberg (CH); William Lutz, Riehen (CH); Peter Maienfisch, Rodersdorf (CH); Werner Zambach, Baettwil (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 694 days.

(21) Appl. No.: 12/440,895

(22) PCT Filed: Sep. 7, 2007

(86) PCT No.: PCT/EP2007/007813
§ 371 (c)(1),
(2), (4) Date: Nov. 18, 2009

(87) PCT Pub. No.: WO2008/031534
PCT Pub. Date: Mar. 20, 2008

(65) Prior Publication Data
US 2010/0076078 A1  Mar. 25, 2010

(30) Foreign Application Priority Data

Sep. 11, 2006 (GB) .................................. 0617858.6
Oct. 2, 2006 (GB) .................................. 0619412.0

(51) Int. Cl.
*C07D 213/61* (2006.01)
*A01N 43/34* (2006.01)

(52) U.S. Cl.
USPC ............ 514/357; 514/616; 546/316; 564/152

(58) Field of Classification Search
None
See application file for complete search history.

(56) References Cited

U.S. PATENT DOCUMENTS 5,629,124 A  5/1997  Ono et al.

FOREIGN PATENT DOCUMENTS

| EP | 1006102 A2 | 6/2000 |
|---|---|---|
| JP | 09278731 | 10/1997 |
| JP | 2006225340 | 8/2006 |
| JP | 2006306771 | 11/2006 |
| JP | 2006306850 | 11/2006 |
| JP | 2007099761 | 4/2007 |
| JP | 2007302617 | 11/2007 |
| WO | 9708135 | 3/1997 |
| WO | 9841513 | 9/1998 |
| WO | 9932433 | 7/1999 |
| WO | 9955663 | 11/1999 |
| WO | 00/07991 A | 2/2000 |
| WO | 0007980 | 2/2000 |
| WO | 0035942 | 6/2000 |
| WO | 0055120 | 9/2000 |
| WO | 0119788 | 3/2001 |
| WO | WO 01/14339 A2 * | 3/2001 |
| WO | WO 01/21160 A2 * | 3/2001 |
| WO | 0146124 | 6/2001 |
| WO | 0156962 | 8/2001 |
| WO | 03006469 | 1/2003 |
| WO | 03011028 | 2/2003 |
| WO | 03015774 | 2/2003 |
| WO | 2004006906 | 1/2004 |
| WO | 2004018410 | 3/2004 |
| WO | 2004043335 | 5/2004 |
| WO | 2004085419 | 10/2004 |
| WO | 2005021488 | 3/2005 |
| WO | 2005063165 | 8/2005 |
| WO | 2005118579 | 12/2005 |
| WO | WO 2006/027795 A1 * | 3/2006 |
| WO | 2006137376 | 12/2006 |
| WO | 2006137395 | 12/2006 |
| WO | 2007013150 | 2/2007 |
| WO | 2007013332 | 2/2007 |
| WO | 2007017075 | 2/2007 |
| WO | 2007022380 | 2/2007 |
| WO | 2007051560 | 5/2007 |
| WO | 2007069684 | 6/2007 |
| WO | 2007083394 | 7/2007 |
| WO | 2007083411 | 7/2007 |
| WO | 2007128410 | 11/2007 |
| WO | 2008000438 | 1/2008 |
| WO | 2008012027 | 1/2008 |

OTHER PUBLICATIONS

Sieglar E H et al: "Toxicity Tests of Certain N-Substituted Benzamides Against Coding Moth Larvae", Journal of Economic Entomology, Entomological Society of America, Landham, MD, US, vol. 37, No. 3, Jun. 1944, pp. 445-446.

* cited by examiner

*Primary Examiner* — Zinna Northington Davis
(74) *Attorney, Agent, or Firm* — Brian D. McAlhaney

(57) ABSTRACT

Novel compounds of formula (I): wherein $A^1, A^2, A^3, A^4, R^1, R^2, G^1, G^2, Q^1$ and $Q^2$ are as defined in claim 1; or salts or N-oxides thereof. Furthermore, the present invention relates to processes for preparing compounds of formula (I), to insecticidal, acaricidal, molluscicidal and nematicidal compositions comprising them and to methods of using them to combat and control insect, acarine, mollusc and nematode pests.

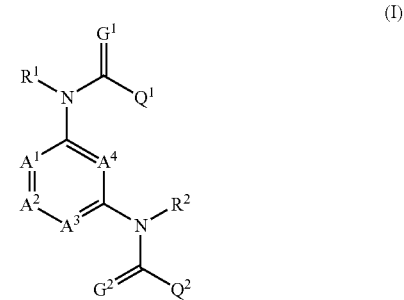

(I)

17 Claims, No Drawings

INSECTICIDAL COMPOUNDS

This application is a 371 of International Application No. PCT/EP2007/007813 filed Sep. 7, 2007, which claims priority to GB 0617858.6 filed Sep. 11, 2006, and GB 0619412.0 filed Oct. 2, 2006, the contents of which are incorporated herein by reference.

The present invention relates to certain bisamide derivatives, to processes and intermediates for preparing them, to insecticidal, acaricidal, molluscicidal and nematicidal compositions comprising them and to methods of using them to combat and control insect, acarine, mollusc and nematode pests.

N,N'-1,3-Phenylene-bis-benzamide (CAS RN 17223-18-6) was disclosed as an insecticide in Journal of Economic Entomology (1944), 37, 445. A bisaziridine carboxamide (CAS RN 2131-75-1) was disclosed as an insecticide, for example, in Journal of Economic Entomology (1964), 57(5), 663-4. Certain biscoumarin carboxamides such as CAS RN 27596-53-8 were disclosed as insecticides in U.S. Pat. No. 3,509,177. Acylamino-s-triazines were disclosed as insecticides, for example, in EP 145660.

N,N'-Meta-bis-anilide derivatives have been disclosed as herbicides in U.S. Pat. No. 4,028,093.

Certain N,N'-meta-bis-carboxamides were disclosed as pharmaceuticals, for example in WO 99/15164, WO 99/59959 and WO 00/007991.

It has now surprisingly been found that certain bisamide derivatives have insecticidal properties.

The present invention therefore provides a compound of formula (I):

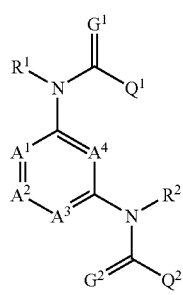

wherein
$A^1, A^2, A^3$ and $A^4$ are independently of one another C—X or nitrogen, provided that no more than two of $A^1, A^2, A^3$ and $A^4$ are nitrogen;
each X is independently hydrogen, halogen, cyano, $C_1$-$C_4$alkyl, $C_1$-$C_4$haloalkyl or $C_1$-$C_4$alkoxy;
$R^1$ and $R^2$ are independently of one another hydrogen, $C_1$-$C_4$alkyl or $C_1$-$C_4$alkylcarbonyl;
$G^1$ and $G^2$ are independently of one another oxygen or sulfur;
$Q^1$ is aryl or aryl substituted by one to five substituents $R^3$, which may be the same or different, or $Q^1$ is heterocyclyl or heterocyclyl substituted by one to five substituents $R^3$, which may be the same or different; wherein
each $R^3$ is independently cyano, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halo-cycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkyl-sulfinyl, $C_1$-$C_3$haloalkylsulfinyl, $C_1$-$C_3$alkylsulfonyl, $C_1$-$C_3$haloalkylsulfonyl, amino, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$alkylcarbonylamino, aryl which is optionally substituted by one to three substituents independently selected from halogen, $C_1$-$C_4$alkyl, $C_1$-$C_4$haloalkyl, $C_1$-$C_4$alkoxy or $C_1$-$C_4$haloalkoxy, or heteroaryl which is optionally substituted by one to three substituents independently selected from halogen, $C_1$-$C_4$alkyl, $C_1$-$C_4$haloalkyl, $C_1$-$C_4$alkoxy or $C_1$-$C_4$haloalkoxy; and
$Q^2$ is a moiety of formula (II) or (III)

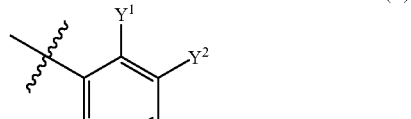

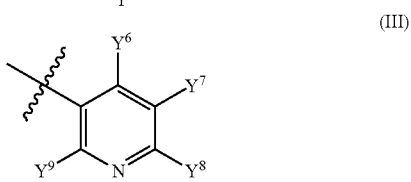

wherein
$Y^1$ and $Y^5$ are independently of each other hydrogen, cyano, halogen, $C_1$-$C_4$alkyl, $C_1$-$C_4$halo-alkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;
$Y^3$ is $C_2$-$C_6$ perfluoroalkyl, $C_1$-$C_6$ perfluoroalkylthio, $C_1$-$C_6$ perfluoroalkylsulfinyl or $C_1$-$C_6$ per-fluoroalkylsulfonyl;
$Y^2$ and $Y^4$ are independently of each other hydrogen, halogen or $C_1$-$C_4$alkyl;
$Y^6$ and $Y^9$ are independently of each other hydrogen, cyano, halogen, $C_1$-$C_4$alkyl, $C_1$-$C_4$halo-alkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_3$haloalkylsulfinyl, $C_1$-$C_3$alkylsulfonyl or $C_1$-$C_3$haloalkylsulfonyl;
$Y^8$ is $C_1$-$C_4$haloalkoxy, $C_2$-$C_6$perfluoroalkyl, $C_1$-$C_6$perfluoroalkylthio, $C_1$-$C_6$perfluoroalkyl-sulfinyl or $C_1$-$C_6$ perfluoroalkylsulfonyl;
$Y^7$ is hydrogen, halogen or $C_1$-$C_4$alkyl;
or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxy-carbonyl, alkylcarbonyl, alkylaminocarbonyl, dialkylaminocarbonyl) is a straight or branched chain and is, for example, methyl, ethyl, n-propyl, n-butyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —CF$_3$, —CF$_2$Cl, —CH$_2$CF$_3$ or —CH$_2$CHF$_2$. Perfluoroalkyl groups (either alone or as part of a larger group, such as perfluoroalkylthio) are a particular type of haloalkyl group; they are alkyl groups which are completely substituted with fluorine atoms and are, for example, —CF$_3$, —CF$_2$CF$_3$ or —CF(CF$_3$)$_2$.

Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=CF$_2$, —CCl=CClF or —CHClC≡CH.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

Halocycloalkyl groups are cycloalkyl groups which are substituted with one or more of the same or different halogen atoms and may optionally be substituted by one or more methyl groups. Examples of monocyclic halocycloalkyl groups are 2,2-dichloro-cyclopropyl, 2,2-dichloro-1-methyl-cyclopropyl and 2-chloro-4-fluorocyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl (for example, 4-amino-phenyl, biphenyl-4-yl, 5-bromo-2-hydroxy-phenyl, 2-bromo-phenyl, 3-chloro-2-fluoro-phenyl, 5-chloro-2-fluoro-phenyl, 3-chloro-2-hydroxy-phenyl, 3-chloro-2-methyl-phenyl, 2-chloro-5-nitro-phenyl, 2-chloro-phenyl, 3-chloro-phenyl, 3-chloro-2,4,5-trifluoro-phenyl, 4-cyano-2-fluoro-phenyl, 4-cyano-phenyl, 2,5-dichloro-phenyl, 2,6-diethyl-4-per-fluoroisopropyl-phenyl, 2,3-difluoro-phenyl, 4-(N',N'-dimethylamino)-phenyl, 3-fluoro-4-hydroxy-phenyl, 2-fluoro-4-nitro-phenyl, 3-fluoro-4-nitro-phenyl, 2-fluoro-phenyl, 3-fluoro-phenyl, 4-fluoro-phenyl, 2-fluoro-3-trifluoromethyl-phenyl, 2-fluoro-5-trifluoromethyl-phenyl, 4-fluoro-3-trifluoromethyl-phenyl, 4-methoxycarbonyl-phenyl, 2-methoxy-phenyl, 4-methoxy-phenyl, 2-methyl-phenyl, 3-methyl-phenyl, 4-methyl-phenyl, 4-methylthio-phenyl, 2-methylthio-4-trifluoromethyl-phenyl, 2-nitro-phenyl, 3-nitro-phenyl, 4-nitro-phenyl, phenyl, 4-(prop-2'-yl)-phenyl, 4-(pyrrol-1'-yl)-phenyl, 4-(1,2,3-thiadiazol-4'-yl)-phenyl, 2-trifluoromethoxy-phenyl, 4-trifluoromethoxy-phenyl, 2-trifluoromethyl-phenyl and 4-trifluoromethyl-phenyl).

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl (for example, 5-bromo-pyrid-3-yl, 2-chloro-pyrid-3-yl, 2-chloro-pyrid-4-yl, 6-chloro-pyrid-3-yl, 3-chloro-5-trifluoromethyl-pyrid-2-yl, 2-fluoro-pyrid-3-yl, 3-fluoro-pyrid-4-yl, 3-methyl-pyrid-2-yl, 2-methylthio-pyrid-3-yl, pyrid-3-yl and pyrid-4-yl), pyridazinyl, pyrimidyl (for example, pyrimid-5-yl, such as 4-methyl-2-phenyl-pyrimid-5-yl), pyrazinyl, furanyl (for example, furan-2-yl, such as 5-bromo-furan-2-yl, furan-2-yl and 5-phenyl-furan-2-yl), thiophenyl (for example, thiophen-2-yl, such as 5-chloro-thiophen-2-yl, 5-(pyrid-2'-yl)-thiophen-2-yl and thiophen-2-yl and thiophen-3-yl, such as 4-methoxy-thiophen-3-yl), oxazolyl (for example, oxazol-4-yl, such as 5-phenyl-oxazol-4-yl), isoxazolyl (for example, isoxazol-4-yl, such as 5-methyl-3-phenyl-isoxazol-4-yl), oxadiazolyl, thiazolyl (for example, thiazol-5-yl, such as 4-methyl-2-phenyl-thiazol-5-yl), isothiazolyl, thiadiazolyl (for example, 1,2,3-thiadiazol-4-yl and 1,2,3-thiadiazol-5-yl, such as 4-methyl-1,2,3-thiadiazol-5-yl), pyrrolyl (for example, pyrrol-3-yl, such as 1,2,5-trimethyl-1H-pyrrol-3-yl, and pyrrol-4-yl, such as 1-methyl-3-trifluoromethyl-1H-pyrrol-4-yl), pyrazolyl (for example, pyrazol-3-yl, such as 2,5-dimethyl-2H-pyrazol-3-yl and 2-(3'-chloro-pyrid-2'-yl)-5-trifluoromethyl-2H-pyrazol-3-yl, and pyrazol-4-yl, such as 5-methyl-1-phenyl-1H-pyrazol-4-yl and 1-methyl-3-trifluoromethyl-1H-pyrazol-4-yl), imidazolyl (for example, imidazol-4-yl, such as 1H-imidazol-4-yl), triazolyl and tetrazolyl. A preferred heteroaryl group is pyridine. Examples of bicyclic groups are benzothiophenyl (for example, benzo[b]thiophen-5-yl), benzimidazolyl (for example, 1H-benzimidazol-5-yl), benzothiadiazolyl (for example, benzo[1,2,5]-thiadiazol-5-yl), quinolinyl (for example, quinolin-2-yl), cinnolinyl (for example, cinnolin-4-yl), quinoxalinyl (for example, quinoxalin-2-yl) and pyrazolo[1,5-a]pyrimidyl (for example, pyrazolo[1,5-a]pyrimid-6-yl, such as 2,7-dimethyl-pyrazolo[1,5-a]pyrimid-6-yl). The structures of some of the heteroaryl moieties are as follows:

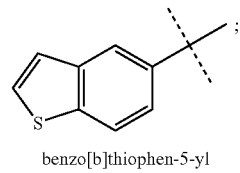

benzo[b]thiophen-5-yl

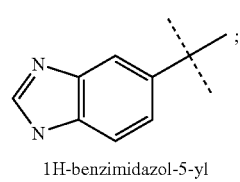

1H-benzimidazol-5-yl

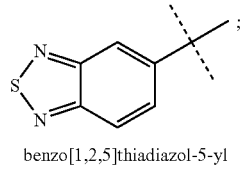

benzo[1,2,5]thiadiazol-5-yl

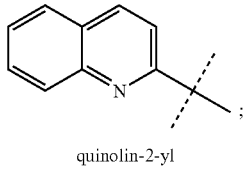

quinolin-2-yl

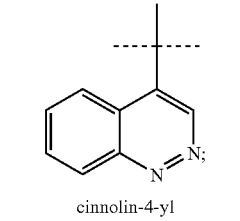

cinnolin-4-yl

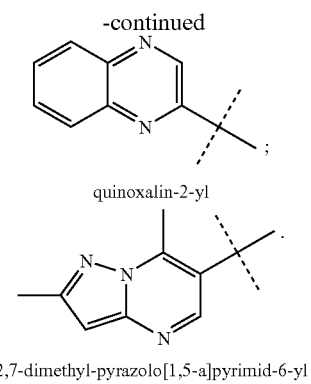

quinoxalin-2-yl 2,7-dimethyl-pyrazolo[1,5-a]pyrimid-6-yl

The term "heterocyclyl" is defined to include heteroaryl and in addition their unsaturated or partially unsaturated analogues such as piperidinyl, 1,3-dioxolanyl, 1,3-dioxanyl, 4,5-dihydro-isoxazolyl, tetrahydrofuranyl and morpholinyl. Examples of bicyclic groups are 4,5,6,7-tetrahydro-benzothiophenyl (for example, 4,5,6,7-tetrahydro-benzo[c]thiophen-1-yl), 3,4-dihydro-2H-benzo-1,4-dioxepinyl (for example, 3,4-dihydro-2H-benzo[b][1,4]dioxepin-7-yl), 2,3-dihydro-benzofuranyl (for example, 2,3-dihydro-benzofuran-5-yl). The structures of these heterocyclyl moieties are as follows:

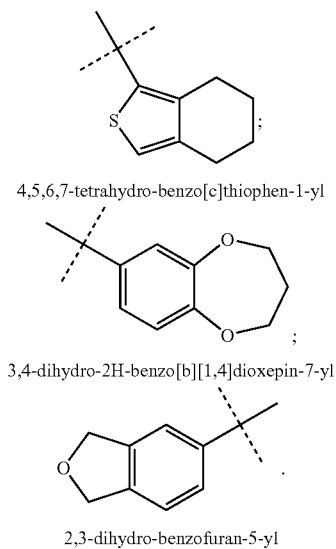

4,5,6,7-tetrahydro-benzo[c]thiophen-1-yl 3,4-dihydro-2H-benzo[b][1,4]dioxepin-7-yl 2,3-dihydro-benzofuran-5-yl Preferred values of $A^1$, $A^2$, $A^3$, $A^4$, X, $R^2$, $G^1$, $G^2$, $Q^1$, $Q^2$, $Y^1$, $Y^2$, $Y^3$, $Y^4$, $Y^5$, $Y^6$, $Y^7$, $Y^8$ and $Y^9$ are, in any combination, as set out below.

Preferably $A^1$ is C—X.
Preferably $A^2$ is C—X.
Preferably $A^3$ is C—X.
Preferably $A^4$ is C—X.
Preferably each X is independently hydrogen, fluoro, chloro, bromo, cyano, methyl, trifluoromethyl or methoxy.
More preferably each X is independently hydrogen, fluoro, chloro, bromo, cyano, methyl or trifluoromethyl.
Even more preferably each X is independently hydrogen, fluoro, methyl or trifluoromethyl.
Yet even more preferably each X is independently hydrogen or fluoro.
Most preferably each X is hydrogen.

Preferably $R^1$ is hydrogen, methyl, ethyl or acetyl.
More preferably $R^1$ is hydrogen, methyl or ethyl.
Even more preferably $R^1$ is hydrogen or ethyl.
Most preferably $R^1$ is hydrogen.
Preferably $R^2$ is hydrogen, methyl, ethyl or acetyl.
More preferably $R^2$ is hydrogen, methyl or ethyl.
Even more preferably $R^2$ is hydrogen or ethyl.
Most preferably $R^2$ is hydrogen.
Preferably $G^1$ is oxygen.
Preferably $G^2$ is oxygen.
Preferably $Q^1$ is phenyl, pyridyl, pyrimidyl, furanyl, thiophenyl, oxazolyl, isoxazolyl, thiazolyl, thiadiazolyl, pyrrolyl, pyrazolyl or imidazolyl, or phenyl, pyridyl, pyrimidyl, furanyl, thiophenyl, oxazolyl, isoxazolyl, thiazolyl, thiadiazolyl, pyrrolyl, pyrazolyl or imidazolyl substituted by one to four substituents independently selected from cyano, nitro, hydroxy, fluoro, chloro, bromo, methyl, trifluoromethyl, methoxy, methylthio, methyl-sulfinyl, methylsulfonyl or phenyl. Examples of preferred groups for $Q^1$ are biphenyl-4-yl, 5-bromo-furan-2-yl, 5-bromo-2-hydroxy-phenyl, 2-bromo-phenyl, 5-bromo-pyrid-3-yl, 3-chloro-2-fluoro-phenyl, 5-chloro-2-fluoro-phenyl, 3-chloro-2-hydroxy-phenyl, 3-chloro-2-methyl-phenyl, 2-chloro-5-nitro-phenyl, 2-chloro-phenyl, 3-chloro-phenyl, 2-chloro-pyrid-3-yl, 2-chloro-pyrid-4-yl, 6-chloro-pyrid-3-yl, 5-chloro-thiophen-2-yl, 3-chloro-2,4,5-trifluoro-phenyl, 3-chloro-5-trifluoromethyl-pyrid-2-yl, 4-cyano-2-fluoro-phenyl, 4-cyano-phenyl, 2,5-dichloro-phenyl, 2,3-difluoro-phenyl, 2,5-dimethyl-2H-pyrazol-3-yl, 3-fluoro-4-hydroxy-phenyl, 2-fluoro-4-nitro-phenyl, 3-fluoro-4-nitro-phenyl, 2-fluoro-phenyl, 3-fluoro-phenyl, 4-fluoro-phenyl, 2-fluoro-pyrid-3-yl, 3-fluoro-pyrid-4-yl, 2-fluoro-3-trifluoromethyl-phenyl, 2-fluoro-5-trifluoromethyl-phenyl, 4-fluoro-3-trifluoromethyl-phenyl, furan-2-yl, 1H-imidazol-4-yl, 2-methoxy-phenyl, 4-methoxy-phenyl, 4-methoxy-thiophen-3-yl, 2-methyl-phenyl, 3-methyl-phenyl, 4-methyl-phenyl, 5-methyl-3-phenyl-isoxazol-4-yl, 5-methyl-1-phenyl-1H-pyrazol-4-yl, 4-methyl-2-phenyl-pyrimid-5-yl, 4-methyl-2-phenyl-thiazol-5-yl, 3-methyl-pyrid-2-yl, 4-methyl-1,2,3-thiadiazol-5-yl, 4-methylthio-phenyl, 2-methylthio-pyrid-3-yl, 2-methylthio-4-trifluoromethyl-phenyl, 1-methyl-3-trifluoromethyl-1H-pyrazol-4-yl, 1-methyl-3-trifluoromethyl-1H-pyrrol-4-yl, 2-nitro-phenyl, 3-nitro-phenyl, 4-nitro-phenyl, phenyl, 5-phenyl-furan-2-yl, 5-phenyl-oxazol-4-yl, pyrid-3-yl, pyrid-4-yl, 1,2,3-thiadiazol-4-yl, 1,2,5-trimethyl-1H-pyrrol-3-yl, thiophen-2-yl, 2-trifluoromethyl-phenyl and 4-trifluoromethyl-phenyl.

More preferably $Q^1$ is phenyl, pyridyl, furanyl, thiophenyl, pyrazolyl or 1,2,3-thiadiazolyl, or phenyl, pyridyl, furanyl, thiophenyl, pyrazolyl or 1,2,3-thiadiazolyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of more preferred groups for $Q^1$ are biphenyl-4-yl, 5-bromo-furan-2-yl, 5-bromo-2-hydroxy-phenyl, 2-bromo-phenyl, 5-bromo-pyrid-3-yl, 3-chloro-2-fluoro-phenyl, 5-chloro-2-fluoro-phenyl, 3-chloro-2-hydroxy-phenyl, 3-chloro-2-methyl-phenyl, 2-chloro-5-nitro-phenyl, 2-chloro-phenyl, 3-chloro-phenyl, 2-chloro-pyrid-3-yl, 2-chloro-pyrid-4-yl, 6-chloro-pyrid-3-yl, 5-chloro-thiophen-2-yl, 3-chloro-5-trifluoro-methyl-pyrid-2-yl, 4-cyano-2-fluoro-phenyl, 4-cyano-phenyl, 2,5-dichloro-phenyl, 2,3-difluoro-phenyl, 2,5-dimethyl-2H-pyrazol-3-yl, 3-fluoro-4-hydroxy-phenyl, 2-fluoro-4-nitro-phenyl, 3-fluoro-4-nitro-phenyl, 2-fluoro-phenyl, 3-fluoro-phenyl, 4-fluoro-phenyl, 2-fluoro-pyrid-3-yl, 3-fluoro-pyrid-4-yl, 2-fluoro-3-trifluoromethyl-phenyl, 2-fluoro-5-trifluoro-methyl-phenyl, 4-fluoro-3-trifluoromethyl-phenyl, furan-2-yl, 2-methoxy-phenyl, 4-methoxy-phenyl, 4-methoxy-thiophen-3-yl, 2-methyl-phenyl, 3-methyl-phenyl, 4-methyl-phenyl, 5-methyl-1-phenyl-1H-pyrazol-4-yl, 3-methyl-pyrid-2-yl, 4-methyl-1,2,3-thiadiazol-5-yl, 4-methylthio-phenyl, 2-methylthio-pyrid-3-yl, 2-methylthio-4-trifluoromethyl-phenyl, 1-methyl-3-trifluoromethyl-1H-pyrazol-4-yl, 2-nitro-phenyl, 3-nitro-phenyl, 4-nitro-phenyl, phenyl, 5-phenyl-furan-2-yl, pyrid-3-yl, pyrid-4-yl, 1,2,3-thiadiazol-4-yl, thiophen-2-yl, 2-trifluoromethyl-phenyl and 4-trifluoromethyl-phenyl.

Even more preferably $Q^1$ is phenyl or pyridyl, or phenyl or pyridyl substituted by one to three substituents independently selected from cyano, hydroxy, fluoro, chloro, methyl, trifluoromethyl, methoxy, methylthio, methylsulfinyl, methylsulfonyl or phenyl. Examples of even more preferred groups for $Q^1$ are biphenyl-4-yl, 3-chloro-2-fluoro-phenyl, 5-chloro-2-fluoro-phenyl, 3-chloro-2-hydroxy-phenyl, 3-chloro-2-methyl-phenyl, 2-chloro-phenyl, 3-chloro-phenyl, 2-chloro-pyrid-3-yl, 2-chloro-pyrid-4-yl, 6-chloro-pyrid-3-yl, 3-chloro-5-trifluoromethyl-pyrid-2-yl, 4-cyano-2-fluoro-phenyl, 4-cyano-phenyl, 2,5-dichloro-phenyl, 2,3-difluoro-phenyl, 3-fluoro-4-hydroxy-phenyl, 2-fluoro-phenyl, 3-fluoro-phenyl, 4-fluoro-phenyl, 2-fluoro-pyrid-3-yl, 3-fluoro-pyrid-4-yl, 2-fluoro-3-trifluoromethyl-phenyl, 2-fluoro-5-trifluoromethyl-phenyl, 4-fluoro-3-trifluoromethyl-phenyl, 2-methoxy-phenyl, 4-methoxy-phenyl, 2-methyl-phenyl, 3-methyl-phenyl, 4-methyl-phenyl, 3-methyl-pyrid-2-yl, 4-methylthio-phenyl, 2-methylthio-pyrid-3-yl, 2-methylthio-4-trifluoromethyl-phenyl, phenyl, pyrid-3-yl, pyrid-4-yl, 2-trifluoromethyl-phenyl and 4-trifluoromethyl-phenyl.

Yet even more preferably $Q^1$ is phenyl substituted by one substituent selected from cyano, fluoro or chloro. Examples of yet even more preferred groups for $Q^1$ are 2-chloro-phenyl, 3-chloro-phenyl, 4-cyano-phenyl, 2-fluoro-phenyl, 3-fluoro-phenyl and 4-fluoro-phenyl.

Most preferably $Q^1$ is 4-fluoro-phenyl.

In one preferred embodiment, $Q^1$ is aryl or aryl substituted by one to five substituents $R^3$, which may be the same or different.

Preferably $Q^1$ is phenyl or phenyl substituted by one to four substituents independently selected from cyano, nitro, hydroxy, fluoro, chloro, bromo, methyl, trifluoromethyl, methoxy, methylthio, methylsulfinyl, methylsulfonyl or phenyl. Examples of preferred groups for $Q^1$ are biphenyl-4-yl, 5-bromo-2-hydroxy-phenyl, 2-bromo-phenyl, 3-chloro-2-fluoro-phenyl, 5-chloro-2-fluoro-phenyl, 3-chloro-2-hydroxy-phenyl, 3-chloro-2-methyl-phenyl, 2-chloro-5-nitro-phenyl, 2-chloro-phenyl, 3-chloro-phenyl, 3-chloro-2,4,5-trifluoro-phenyl, 4-cyano-2-fluoro-phenyl, 4-cyano-phenyl, 2,5-dichloro-phenyl, 2,3-difluoro-phenyl, 3-fluoro-4-hydroxy-phenyl, 2-fluoro-4-nitro-phenyl, 3-fluoro-4-nitro-phenyl, 2-fluoro-phenyl, 3-fluoro-phenyl, 4-fluoro-phenyl, 2-fluoro-3-trifluoromethyl-phenyl, 2-fluoro-5-trifluoromethyl-phenyl, 4-fluoro-3-trifluoromethyl-phenyl, 2-methoxy-phenyl, 4-methoxy-phenyl, 2-methyl-phenyl, 3-methyl-phenyl, 4-methyl-phenyl, 4-methylthio-phenyl, 2-methylthio-4-trifluoromethyl-phenyl, 2-nitro-phenyl, 3-nitro-phenyl, 4-nitro-phenyl, phenyl, 2-trifluoromethyl-phenyl and 4-trifluoromethyl-phenyl.

More preferably $Q^1$ is phenyl or phenyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of more preferred groups for $Q^1$ are biphenyl-4-yl, 5-bromo-2-hydroxy-phenyl, 2-bromo-phenyl, 3-chloro-2-fluoro-phenyl, 5-chloro-2-fluoro-phenyl, 3-chloro-2-hydroxy-phenyl, 3-chloro-2-methyl-phenyl, 2-chloro-5-nitro-phenyl, 2-chloro-phenyl, 3-chloro-phenyl, 3-chloro-5-trifluoromethyl-pyrid-2-yl, 4-cyano-2-fluoro-phenyl, 4-cyano-phenyl, 2,5-dichloro-phenyl, 2,3-difluoro-phenyl, 3-fluoro-4-hydroxy-phenyl, 2-fluoro-4-nitro-phenyl, 3-fluoro-4-nitro-phenyl, 2-fluoro-phenyl, 3-fluoro-phenyl, 4-fluoro-phenyl, 2-fluoro-3-trifluoromethyl-phenyl, 2-fluoro-5-trifluoromethyl-phenyl, 4-fluoro-3-trifluoromethyl-phenyl, 2-methoxy-phenyl, 4-methoxy-phenyl, 2-methyl-phenyl, 3-methyl-phenyl, 4-methyl-phenyl, 4-methylthio-phenyl, 2-methylthio-4-trifluoromethyl-phenyl, 2-nitro-phenyl, 3-nitro-phenyl, 4-nitro-phenyl, phenyl, 2-trifluoromethyl-phenyl and 4-trifluoromethyl-phenyl.

Even more preferably $Q^1$ is phenyl or phenyl substituted by one to three substituents independently selected from cyano, hydroxy, fluoro, chloro, methyl, trifluoromethyl, methoxy, methylthio, methylsulfinyl, methylsulfonyl or phenyl. Examples of even more preferred groups for $Q^1$ are biphenyl-4-yl, 3-chloro-2-fluoro-phenyl, 5-chloro-2-fluoro-phenyl, 3-chloro-2-hydroxy-phenyl, 3-chloro-2-methyl-phenyl, 2-chloro-phenyl, 3-chloro-phenyl, 4-cyano-2-fluoro-phenyl, 4-cyano-phenyl, 2,5-dichloro-phenyl, 2,3-difluoro-phenyl, 3-fluoro-4-hydroxy-phenyl, 2-fluoro-phenyl, 3-fluoro-phenyl, 4-fluoro-phenyl, 2-fluoro-3-trifluoromethyl-phenyl, 2-fluoro-5-trifluoromethyl-phenyl, 4-fluoro-3-trifluoromethyl-phenyl, 2-methoxy-phenyl, 4-methoxy-phenyl, 2-methyl-phenyl, 3-methyl-phenyl, 4-methyl-phenyl, 4-methylthio-phenyl, 2-methylthio-4-trifluoromethyl-phenyl, phenyl, 2-trifluoromethyl-phenyl and 4-trifluoromethyl-phenyl.

In one preferred embodiment $Q^1$ is heterocyclyl or heterocyclyl substituted by one to five substituents $R^3$, which may be the same or different.

In a further preferred embodiment $Q^1$ is heteroaryl or heteroaryl substituted by one to five substituents $R^3$, which may be the same or different.

Preferably $Q^1$ is pyridyl, pyrimidyl, furanyl, thiophenyl, oxazolyl, isoxazolyl, thiazolyl, thiadiazolyl, pyrrolyl, pyrazolyl or imidazolyl, or pyridyl, pyrimidyl, furanyl, thiophenyl, oxazolyl, isoxazolyl, thiazolyl, thiadiazolyl, pyrrolyl, pyrazolyl or imidazolyl substituted by one to four substituents independently selected from cyano, nitro, hydroxy, fluoro, chloro, bromo, methyl, trifluoromethyl, methoxy, methylthio, methylsulfinyl, methylsulfonyl or phenyl. Examples of preferred groups for $Q^1$ are 5-bromo-furan-2-yl, 5-bromo-pyrid-3-yl, 2-chloro-pyrid-3-yl, 2-chloro-pyrid-4-yl, 6-chloro-pyrid-3-yl, 5-chloro-thiophen-2-yl, 3-chloro-5-trifluoromethyl-pyrid-2-yl, 2,5-dimethyl-2H-pyrazol-3-yl, 2-fluoro-pyrid-3-yl, 3-fluoro-pyrid-4-yl, furan-2-yl, 1H-imidazol-4-yl, 4-methoxy-thiophen-3-yl, 5-methyl-3-phenyl-isoxazol-4-yl, 5-methyl-1-phenyl-1H-pyrazol-4-yl, 4-methyl-2-phenyl-pyrimid-5-yl, 4-methyl-2-phenyl-thiazol-5-yl, 3-methyl-pyrid-2-yl, 4-methyl-1,2,3-thiadiazol-5-yl, 2-methylthio-pyrid-3-yl, 1-methyl-3-trifluoromethyl-1H-pyrazol-4-yl, 1-methyl-3-trifluoromethyl-1H-pyrrol-4-yl, 5-phenyl-furan-2-yl, 5-phenyl-oxazol-4-yl, pyrid-3-yl, pyrid-4-yl, 1,2,3-thiadiazol-4-yl, 1,2,5-trimethyl-1H-pyrrol-3-yl and thiophen-2-yl.

More preferably $Q^1$ is pyridyl, furanyl, thiophenyl, pyrazolyl or 1,2,3-thiadiazolyl, or pyridyl, furanyl, thiophenyl, pyrazolyl or 1,2,3-thiadiazolyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of more preferred groups for $Q^1$ are 5-bromo-furan-2-yl, 5-bromo-pyrid-3-yl, 2-chloro-pyrid-3-yl, 2-chloro-pyrid-4-yl, 6-chloro-pyrid-3-yl, 5-chloro-thiophen- 2-yl, 3-chloro-5-trifluoromethyl-pyrid-2-yl, 2,5-dimethyl-2H-pyrazol-3-yl, 2-fluoro-pyrid-3-yl, 3-fluoro-pyrid-4-yl, furan-2-yl, 4-methoxy-thiophen-3-yl, 5-methyl-1-phenyl-1H-pyrazol-4-yl, 3-methyl-pyrid-2-yl, 4-methyl-1,2,3-thiadiazol-5-yl, 2-methylthio-pyrid-3-yl, 1-methyl-3-trifluoromethyl-1H-pyrazol-4-yl, 5-phenyl-furan-2-yl, pyrid-3-yl, pyrid-4-yl, 1,2,3-thiadiazol-4-yl and thiophen-2-yl.

Even more preferably $Q^1$ is pyridyl or pyridyl substituted by one to three substituents independently selected from cyano, hydroxy, fluoro, chloro, methyl, trifluoromethyl, methoxy, methylthio, methylsulfinyl, methylsulfonyl or phenyl. Examples of even more preferred groups for $Q^1$ are 2-chloro-pyrid-3-yl, 2-chloro-pyrid-4-yl, 6-chloro-pyrid-3-yl, 3-chloro-5-trifluoromethyl-pyrid-2-yl, 2-fluoro-pyrid-3-yl, 3-fluoro-pyrid-4-yl, 3-methyl-pyrid-2-yl, 2-methylthio-pyrid-3-yl, pyrid-3-yl and pyrid-4-yl.

Preferably $Q^2$ is a moiety of formula (II).

Preferably $Y^1$ is cyano, chloro, bromo, methyl, ethyl, trifluoromethyl or methoxymethyl.

More preferably $Y^1$ is cyano, chloro, bromo, methyl or trifluoromethyl.

Even more preferably $Y^1$ is methyl or ethyl.

Most preferably $Y^1$ is methyl.

Preferably $Y^2$ is hydrogen, fluoro, chloro or methyl.

Most preferably $Y^2$ is hydrogen.

Preferably $Y^3$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.

Most preferably $Y^3$ is heptafluoroprop-2-yl.

Preferably $Y^4$ is hydrogen, fluoro, chloro or methyl.

Most preferably $Y^4$ is hydrogen.

Preferably $Y^5$ is cyano, chloro, bromo, methyl, ethyl or trifluoromethyl.

More preferably $Y^5$ is cyano, chloro, bromo, methyl or trifluoromethyl.

Even more preferably $Y^5$ is methyl or ethyl.

Most preferably $Y^5$ is methyl.

Preferably $Y^6$ is cyano, chloro, bromo, methyl, ethyl, trifluoromethyl or methoxymethyl.

More preferably $Y^6$ is cyano, chloro, bromo, methyl or trifluoromethyl.

Even more preferably $Y^6$ is methyl or ethyl.

Most preferably $Y^6$ is methyl.

Preferably $Y^7$ is hydrogen, fluoro, chloro or methyl.

Most preferably $Y^7$ is hydrogen.

Preferably $Y^8$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.

Most preferably $Y^8$ is heptafluoroprop-2-yl.

Preferably $Y^9$ is cyano, chloro, bromo, methyl, ethyl, trifluoromethyl or methoxymethyl.

More preferably $Y^9$ is cyano, chloro, bromo, methyl or trifluoromethyl.

Even more preferably $Y^9$ is methyl or ethyl.

Most preferably $Y^9$ is methyl.

One preferred embodiment are compounds of formula (Ia) wherein $A^1, A^2, A^3, A^4$ are CH.

Another preferred embodiment are compounds of formula (Ib) wherein $A^1$ is C—F, and $A^2, A^3$, and $A^4$ are CH.

A further preferred embodiment are compounds of formula (Ic) wherein $A^2$ is C—F, and $A^1, A^3$, and $A^4$ are CH.

Yet another preferred embodiment are compounds of formula (Id) wherein $A^3$ is C—F, and $A^1, A^2$, and $A^4$ are CH.

Yet a further preferred embodiment are compounds of formula (Ie) wherein $A^4$ is C—F, and $A^1, A^2$, and $A^3$ are CH.

Another preferred embodiment are compounds of formula (If) wherein $A^1$ is C—CN, and $A^2, A^3$, and $A^4$ are CH.

A further preferred embodiment are compounds of formula (Ig) wherein $A^2$ is C—CN, and $A^1, A^3$, and $A^4$ are CH.

Yet another preferred embodiment are compounds of formula (Ih) wherein $A^3$ is C—CN, and $A^1, A^2$, and $A^4$ are CH.

Yet a further preferred embodiment are compounds of formula (Ij) wherein $A^4$ is C—CN, and $A^1, A^2$, and $A^3$ are CH.

One preferred embodiment are compounds of formula (I) wherein $Q^2$ is 2,6-dimethyl-4-perfluoroisopropyl-phenyl.

Another preferred embodiment are compounds of formula (I) wherein $Q^2$ is 2-ethyl-6-methyl-4-perfluoroisopropyl-phenyl.

A further preferred embodiment are compounds of formula (I) wherein $Q^2$ is 2,6-diethyl-4-perfluoroisopropyl-phenyl.

Yet another preferred embodiment are compounds of formula (I) wherein $Q^2$ is 2-methoxymethyl-6-methyl-4-perfluoroisopropyl-phenyl.

Yet another preferred embodiment are compounds of formula (I) wherein $Q^2$ is 2-methyl-4-perfluoroisopropyl-phenyl.

In one preferred embodiment, each X is independently hydrogen, halogen, $C_1$-$C_4$alkyl or trifluoromethyl.

In one preferred embodiment, $Q^1$ is aryl or aryl substituted by one to five substituents $R^3$, which may be the same or different, or $Q^1$ is heteroaryl or heteroaryl substituted by one to five substituents $R^3$, which may be the same or different.

In one preferred embodiment, each $R^3$ is independently cyano, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkyl-sulfonyl, $C_1$-$C_3$haloalkylsulfonyl, $C_1$-$C_4$alkylamino, di-($C_1$-$C_4$alkyl)amino, $C_1$-$C_4$alkyl-carbonyl, $C_1$-$C_4$alkylcarbonyloxy, $C_1$-$C_4$alkoxycarbonyl, $C_1$-$C_4$alkylcarbonylamino or phenyl.

In one preferred embodiment, $Y^1$ and $Y^5$ are independently of each other cyano, halogen, $C_1$-$C_4$alkyl, $C_1$-$C_4$haloalkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl.

In one preferred embodiment, $Y^6$ and $Y^9$ are independently of each other cyano, halogen, $C_1$-$C_4$alkyl, $C_1$-$C_4$haloalkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl.

Certain intermediates are novel and as such form a further aspect of the invention. One group of novel intermediates are compounds of formula (VIII')

(VIII')

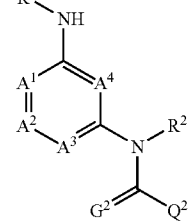

wherein $A^1, A^2, A^3, A^4, R^1, R^2, G^2$ and $Q^2$ are as defined in relation to formula (I); or salts or N-oxides thereof.

The compounds in Tables 1 to 15 below illustrate the compounds of the invention.

Table 1:

Table 1 provides 25 compounds of formula (Ia) wherein $Q^2$ is 2,6-dimethyl-4-perfluoroisopropyl-phenyl and $Q^1$ has the values listed in the table below.

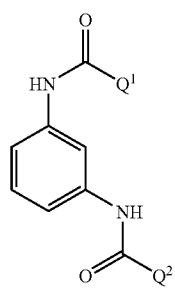

(Ia)

| Compound numbers | $Q^1$ |
|---|---|
| 1.01 | 5-bromo-furan-2-yl |
| 1.02 | 2-bromo-phenyl |
| 1.03 | 5-bromo-pyrid-3-yl |
| 1.04 | 2-chloro-5-nitro-phenyl |
| 1.05 | 2-chloro-phenyl |
| 1.06 | 3-chloro-phenyl |
| 1.07 | 2-chloro-pyrid-3-yl |
| 1.08 | 2-chloro-pyrid-4-yl |
| 1.09 | 6-chloro-pyrid-3-yl |
| 1.10 | 5-chloro-thiophen-2-yl |
| 1.11 | 3-chloro-5-trifluoromethyl-pyrid-2-yl |
| 1.12 | 4-cyano-phenyl |
| 1.13 | 2,5-dichloro-phenyl |
| 1.14 | 2,3-difluoro-phenyl |
| 1.15 | 1,3-dimethyl-pyrazol-5-yl |
| 1.16 | 4-fluoro-phenyl |
| 1.17 | 2-fluoro-pyrid-3-yl |
| 1.18 | 2-fluoro-3-trifluoromethyl-phenyl |
| 1.19 | 2-methyl-phenyl |
| 1.20 | 3-methyl-pyrid-2-yl |
| 1.21 | 2-methylthio-pyrid-3-yl |
| 1.22 | 4-nitro-phenyl |
| 1.23 | phenyl |
| 1.24 | 1,2,3-thiadiazol-4-yl |
| 1.25 | thiophen-2-yl |

Table 2:

Table 2 provides 25 compounds of formula (Ia) wherein $Q^2$ is 2-methyl-4-perfluoro-isopropyl-phenyl and $Q^1$ has the values listed in Table 1.

Table 3:

Table 3 provides 25 compounds of formula (Ia) wherein $Q^2$ is 2,6-diethyl-4-perfluoro-isopropyl-phenyl and $Q^1$ has the values listed in Table 1.

Table 4:

Table 4 provides 25 compounds of formula (Ib) wherein $Q^2$ is 2,6-dimethyl-4-perfluoro-isopropyl-phenyl and $Q^1$ has the values listed in Table 1.

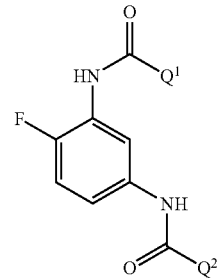

(Ib)

Table 5:

Table 5 provides 25 compounds of formula (Ib) wherein $Q^2$ is 2-methyl-4-perfluoro-isopropyl-phenyl and $Q^1$ has the values listed in Table 1.

Table 6:

Table 6 provides 25 compounds of formula (Ib) wherein $Q^2$ is 2,6-diethyl-4-perfluoro-isopropyl-phenyl and $Q^1$ has the values listed in Table 1.

Table 7:

Table 7 provides 25 compounds of formula (Ic) wherein $Q^2$ is 2,6-dimethyl-4-perfluoro-isopropyl-phenyl and $Q^1$ has the values listed in Table 1.

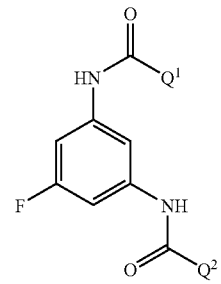

(Ic)

Table 8:

Table 8 provides 25 compounds of formula (Ic) wherein $Q^2$ is 2-methyl-4-perfluoro-isopropyl-phenyl and $Q^1$ has the values listed in Table 1.

Table 9:

Table 9 provides 25 compounds of formula (Ic) wherein $Q^2$ is 2,6-diethyl-4-perfluoro-isopropyl-phenyl and $Q^1$ has the values listed in Table 1.

Table 10:

Table 10 provides 25 compounds of formula (Id) wherein $Q^2$ is 2,6-dimethyl-4-perfluoro-isopropyl-phenyl and $Q^1$ has the values listed in Table 1.

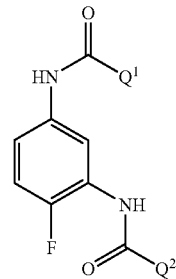

(Id)

Table 11:

Table 11 provides 25 compounds of formula (Id) wherein $Q^2$ is 2-methyl-4-perfluoro-isopropyl-phenyl and $Q^1$ has the values listed in Table 1.

Table 12:

Table 12 provides 25 compounds of formula (Id) wherein $Q^2$ is 2,6-diethyl-4-perfluoro-isopropyl-phenyl and $Q^1$ has the values listed in Table 1.

Table 13:

Table 13 provides 25 compounds of formula (Ie) wherein $Q^2$ is 2,6-dimethyl-4-perfluoro-isopropyl-phenyl and $Q^1$ has the values listed in Table 1.

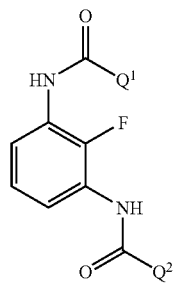

(Ie)

Table 14:

Table 14 provides 25 compounds of formula (Ie) wherein $Q^2$ is 2-methyl-4-perfluoro-isopropyl-phenyl and $Q^1$ has the values listed in Table 1.

Table 15:

Table 15 provides 25 compounds of formula (Ie) wherein $Q^2$ is 2,6-diethyl-4-perfluoro-isopropyl-phenyl and $Q^1$ has the values listed in Table 1.

Table 16:

Table 16 provides 25 compounds of formula (If) wherein $Q^2$ is 2,6-dimethyl-4-perfluoro-isopropyl-phenyl and $Q^1$ has the values listed in Table 1.

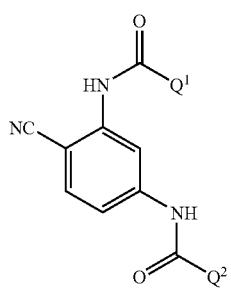

(If)

Table 17:

Table 17 provides 25 compounds of formula (If) wherein $Q^2$ is 2-methyl-4-perfluoro-isopropyl-phenyl and $Q^1$ has the values listed in Table 1.

Table 18:

Table 18 provides 25 compounds of formula (If) wherein $Q^2$ is 2,6-diethyl-4-perfluoro-isopropyl-phenyl and $Q^1$ has the values listed in Table 1.

Table 19:

Table 19 provides 25 compounds of formula (Ig) wherein $Q^2$ is 2,6-dimethyl-4-perfluoro-isopropyl-phenyl and $Q^1$ has the values listed in Table 1.

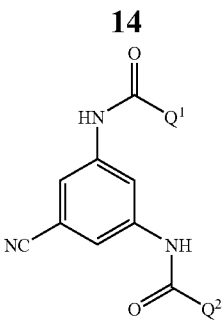

(Ig)

Table 20:

Table 20 provides 25 compounds of formula (Ig) wherein $Q^2$ is 2-methyl-4-perfluoro-isopropyl-phenyl and $Q^1$ has the values listed in Table 1.

Table 21:

Table 21 provides 25 compounds of formula (Ig) wherein $Q^2$ is 2,6-diethyl-4-perfluoro-isopropyl-phenyl and $Q^1$ has the values listed in Table 1.

Table 22:

Table 22 provides 25 compounds of formula (Ih) wherein $Q^2$ is 2,6-dimethyl-4-perfluoro-isopropyl-phenyl and $Q^1$ has the values listed in Table 1.

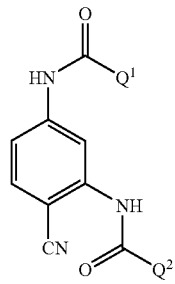

(Ih)

Table 23:

Table 23 provides 25 compounds of formula (Ih) wherein $Q^2$ is 2-methyl-4-perfluoro-isopropyl-phenyl and $Q^1$ has the values listed in Table 1.

Table 24:

Table 24 provides 25 compounds of formula (Ih) wherein $Q^2$ is 2,6-diethyl-4-perfluoro-isopropyl-phenyl and $Q^1$ has the values listed in Table 1.

Table 25:

Table 25 provides 25 compounds of formula (Ij) wherein $Q^2$ is 2,6-dimethyl-4-perfluoro-isopropyl-phenyl and $Q^1$ has the values listed in Table 1.

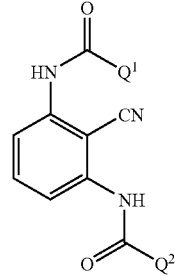

(Ij)

Table 26:

Table 26 provides 25 compounds of formula (Ij) wherein $Q^2$ is 2-methyl-4-perfluoro-isopropyl-phenyl and $Q^1$ has the values listed in Table 1.

Table 27:

Table 27 provides 25 compounds of formula (Ij) wherein $Q^2$ is 2,6-diethyl-4-perfluoro-isopropyl-phenyl and $Q^1$ has the values listed in Table 1.

The compounds of the invention may be made by a variety of methods.

1) Compounds of formula (I), wherein $G^1$ and $G^2$ are oxygen, may be made by sequential treatment of compounds of formula (IV) with a carboxylic acid of formula $Q^1$-COOH or an acid halide of formula $Q^1$-COHal wherein Hal is Cl, F or Br and a carboxylic acid of formula $Q^2$-COOH or an acid halide of formula $Q^2$-COHal wherein Hal is Cl, F or Br. In most cases it is possible for the person skilled in the art to decide in which order $Q^1$ and $Q^2$ are best introduced; it might even be possible to reverse the order in which $Q^1$ and $Q^2$ are introduced.

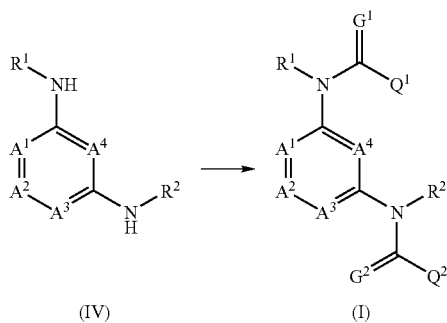

When a carboxylic acid is used such reactions are usually carried out in the presence of a coupling reagent, such as DCC(N,N'-dicyclohexylcarbodiimide), EDC (1-ethyl-3-[3-di-methylamino-propyl]carbodiimide hydrochloride) or BOP-Cl (bis(2-oxo-3-oxazolidinyl)-phosphonic chloride), in the presence of a base, such as pyridine, triethylamine, 4-(dimethyl-amino)-pyridine or diisopropylethylamine, and optionally in the presence of a nucleophilic catalyst, such as hydroxybenzotriazole. When an acid halide is used such reactions are usually carried out under basic conditions (for example in the presence of pyridine, triethyl-amine, 4-(dimethylamino)-pyridine or diisopropylethylamine), again optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate.

2) Acid halides of formula Q-COHal wherein Hal is Cl, F or Br may be made from carboxylic acids of formula Q-COOH under standard conditions, such as treatment with thionyl chloride or oxalyl chloride.

3) Carboxylic acids of formula Q-COOH may be formed from esters of formula Q-COR wherein R is $C_1$-$C_6$alkoxy. It is well known to a person skilled in the art that there are many methods for the hydrolysis of such esters depending on the nature of the alkoxy group. One widely used method to achieve such a transformation is the treatment of the ester with an alkali hydroxide, such as sodium hydroxide, in a solvent, such as ethanol and/or water.

4) Compounds of formula (IV) may be made from compounds of formula (V) by sequential treatment of compound of formula (V) with the alcohols of formula $R^1$—OH and $R^2$—OH under acidic conditions. It is known to a person skilled in the art that there are many reported methods for the formation of this bond depending on the nature of the substituents $R^1$ and $R^2$.

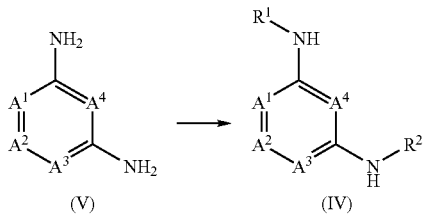

Alternatively, reactions based on oxidized versions of the alcohols such as the corresponding aldehydes and ketones or based on more activated analogues of the alcohols such as the corresponding halides or sulfonates may be used. For example, reductive amination may be achieved by treatment of the amine with an aldehyde or ketone and a reducing agent such as sodium cyanoborohydride. Alternatively alkylation may be achieved by treating the amine with an alkylating agent such as an alkyl halide, optionally in the presence of a base. Alternatively arylation may be achieved by treatment of the amine with an aryl halide or sulfonate in the presence of a suitable catalyst/ligand system, often a palladium (0) complex. Compounds of formula (V) and alcohols of formula $R^1$—OH and $R^2$—OH are either known compounds or may be made by methods known to a person skilled in the art.

5) Alternatively, compounds of formula (IV) may be made from a compound of formula (VI), wherein LG is a leaving group, such as fluoro, chloro, sulfone or sulfonate, via sequential nucleophilic displacement of the leaving groups in a compound of formula (VI) by amines of formula $R^1$—$NH_2$ and $R^2$—$NH_2$. In most cases it is possible for the person skilled in the art to decide in which order $R^1$ and $R^2$ are best introduced; it might even be possible to reverse the order in which $R^1$ and $R^2$ are introduced.

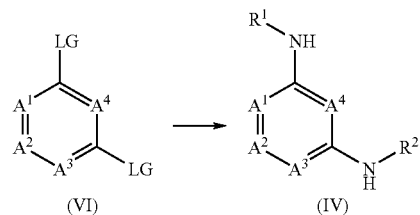

Compounds of formula (VI) and amines of formula $R^1$—$NH_2$ and $R^2$—$NH_2$ are either known compounds or may be made by methods known to a person skilled in the art.

6) Compounds of formula (I), wherein $G^1$ and $G^2$ are sulfur, may be made from a compound of formula (I), wherein $G^1$ and $G^2$ are oxygen, by treatment with a thio-transfer reagent, such as Lawesson's reagent or phosphorus pentasulfide.

7) As indicated above, compounds of formula (I), wherein $G^1$ and $G^2$ are oxygen, may be made by the treatment of compounds of formula (VIII), wherein $G^1$ is oxygen, with a carboxylic acid of formula $Q^2$-COOH or an acid halide of formula $Q^2$-COHal wherein Hal is Cl, F or Br under standard conditions as described in 1).

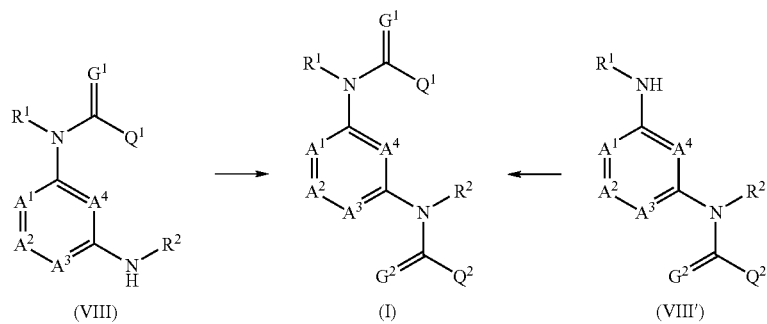

Analogously, compounds of formula (I), wherein $G^1$ and $G^2$ are oxygen, may be made by the treatment of compounds of formula (VIII').

8) Compounds of formula (VIII), wherein $G^1$ is oxygen, may be formed from compounds of formula (VII), wherein P is a suitable protecting group, by amide bond formation with a carboxylic acid of formula $Q^1$-COOH or an acid halide of formula $Q^1$-COHal wherein Hal is Cl, F or Br under standard conditions as described in 1), followed by removal of the protecting group P under standard conditions.

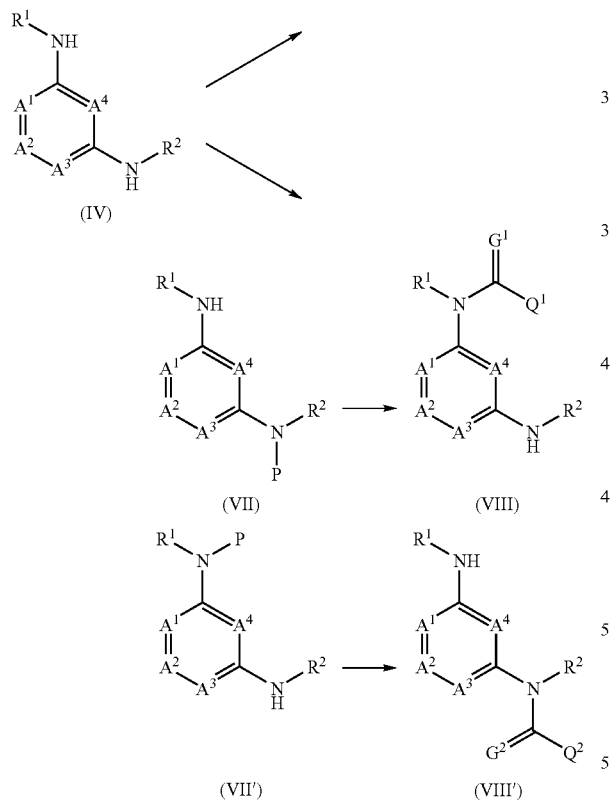

Analogously, compounds of formula (VIII'), wherein $G^2$ is oxygen, may be made by the treatment of compounds of formula (VII').

9) Compounds of formula (VII) may be made by the protection of the amine functionality in compounds of formula (N). Suitable protecting groups include carbamates (such as tert-butyloxycarbonyl, allyloxycarbonyl and benzyloxycarbonyl), trialkylsilyl groups (such as tert-butyldimethylsilyl) and acyl groups (such as acetyl). The formation and removal of such groups is widely reported in the literature and is well known to a person skilled in the art. Analogously, compounds of formula (VII') may be made by the treatment of compounds of formula (IV).

10) Alternatively, compounds of formula (VIII), wherein $G^1$ is oxygen, may be made from compounds of formula (X), wherein $G^1$ is oxygen and LG is a leaving group such as fluoro, chloro or sulfonate, by displacement of the leaving group with a compound of formula $R^2$—$NH_2$. Such reactions are usually performed under basic conditions.

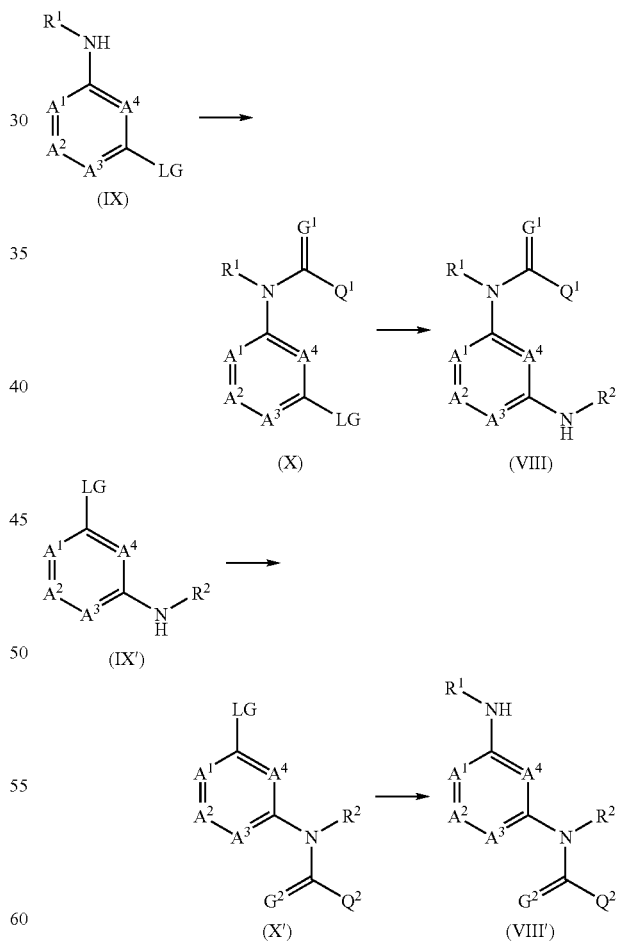

Analogously, compounds of formula (VIII'), wherein $G^2$ is oxygen, may be made by the treatment of compounds of formula (X').

11) Compounds of formula (X) may be made from compounds of formula (IX), wherein LG is a leaving group as described in 10), via amide bond formation with a carboxylic acid of formula $Q^1$-COOH or an acid halide of formula $Q^1$-COHal wherein Hal is Cl, F or Br under standard conditions as described in 1). Analogously, compounds of formula (X') may be made by the treatment of compounds of formula (IX'). Compounds of formula (IX) and compounds of formula (IX') are either known compounds or may be made by methods known to a person skilled in the art.

12) Compounds of formula (I), wherein $G^1$ is sulfur and $G^2$ is oxygen, may be made by treatment of compounds of formula (X), wherein $G^1$ is oxygen and LG is a leaving group, or compounds of formula (VIII), wherein $G^1$ is oxygen, with a thio-transfer reagent such as Lawesson's reagent or phosphorus pentasulfide prior to elaborating to compounds of formula (I), wherein $G^1$ is sulfur and $G^2$ is oxygen, as described in 9) and 7). Analogously, compounds of formula (I), wherein $G^1$ is oxygen and $G^2$ is sulfur, may be made by treatment of compounds of formula (X') or compounds of formula (VIII') with a thio-transfer reagent.

13) An alternative synthesis of compounds of formula (VIII), wherein $G^1$ is oxygen and $R^2$ is hydrogen, may be achieved by the reduction of nitro compounds of formula (XII). There are numerous methods for achieving such a transformation reported in the literature such as treatment with tin chloride under acidic conditions, or hydrogenation catalysed by a noble metal such as palladium on carbon.

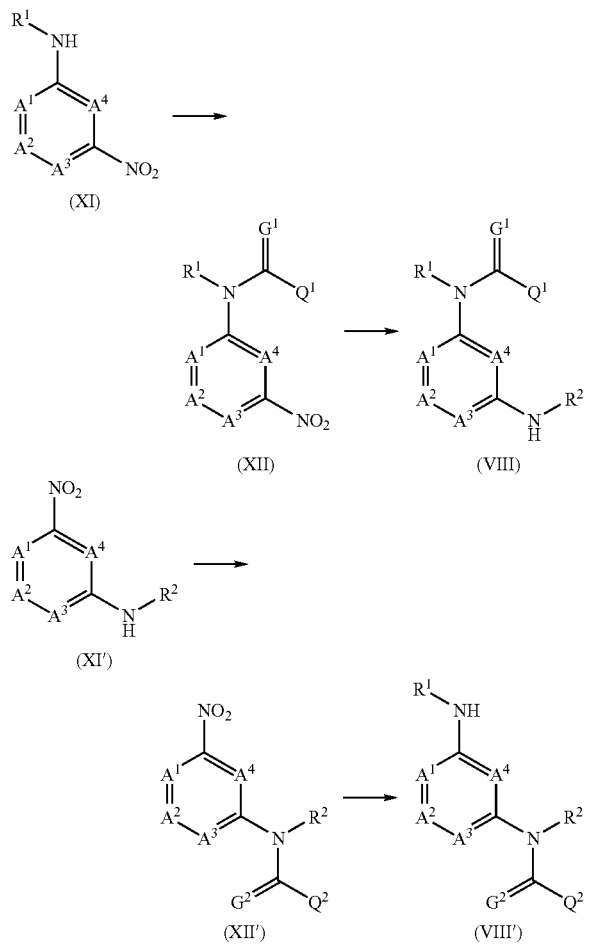

Analogously, compounds of formula (VIII'), wherein $G^2$ is oxygen and $R^1$ is hydrogen, may be made by the treatment of compounds of formula (XII').

14) Compounds of formula (XII), wherein $G^1$ is oxygen, may be derived from compounds of formula (XI) via acylation with a carboxylic acid of formula $Q^1$-COOH or an acid halide of formula $Q^1$-COHal wherein Hal is Cl, F or Br under the standard conditions as described in 1). Analogously, compounds of formula (XII'), wherein $G^2$ is oxygen, may be made by the treatment of compounds of formula (XI'). Compounds of formula (XI) and compounds of formula (XI') are either known or may be made by methods known to a person skilled in the art.

20) Compounds of formula (XI) wherein $R^3$ is cyano, can be made from a compound of formula (XI") wherein LG is halogen, such as fluorine or chlorine, by reaction with a cyanide salt, such as potassium cyanide, in the presence of a base, such as potassium carbonate.

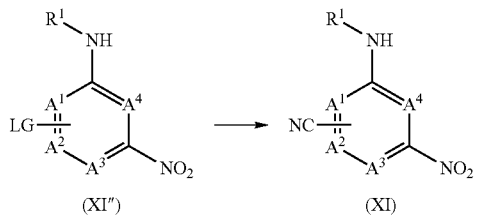

The displacement of a halogen with cyanide can also be carried out on intermediates of formula (XI'), (XII) and (XII').

21) Alternatively, compounds of formula (XI) wherein $R^3$ is cyano, can be made from a compound of formula (XI") wherein LG is halogen, such as iodine or bromine, by reaction with a cyanide salt, such as copper cyanide, via palladium coupling. Such procedure are known, for example, from Bioorganic & Medicinal Chemistry Letters (2005), 15(7), 1895-1899; Angewandte Chemie (1986), 98(12), 1095-9; and Chemistry-A European Journal (2003), 9(8), 1828-1836. The displacement of a halogen by cyanide in a palladium coupling reaction can also be carried out on intermediates of formula (XI'), (XII) and (XII').

22) Furthermore, compounds of formula (XI) wherein $R^3$ is cyano, can be made from a compound of formula (XI") wherein LG is an amine, by reaction with a cyanide salt, such as copper cyanide, via diazotising reaction. The displacement of an amine with cyanide can also be carried out on intermediates of formula (XI'), (XII) and (XII).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogen carbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures preferably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen; or s) Flubendiamid or rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-AI, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 2-iodo-1,3-dimethyl-5-(1,2,2,2-tetrafluoro-1-trifluoromethyl-ethyl)-benzene

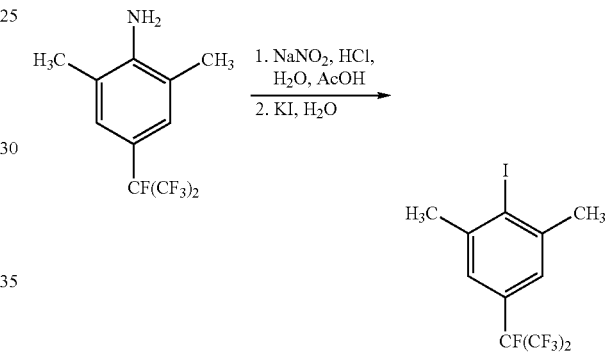

To 4-heptafluoroisopropyl-2,6-dimethylaniline (50 g, 173 mmol) (prepared as described in EP 1006102) in water (600 ml) were successively added acetic acid (12 ml, 173 mmol) and concentrated hydrochloric acid (250 ml). The suspension was cooled to 0° C. and sodium nitrite (13 g) dissolved in water (150 ml) was slowly added. The reaction mixture was stirred for 1 hour at 0° C. before the addition of a solution of sodium iodide (31 g) in water (150 ml). The reaction mixture was heated to 90° C. and stirred for 15-20 minutes at this temperature. The mixture was cooled to ambient temperature and aqueous sodium metabisulfite (saturated) (200 ml) was added. The phases were separated. The aqueous phase was extracted twice with ethyl acetate and the organic phase was washed successively with aqueous sodium hydrogen carbonate (saturated) and with aqueous sodium chloride (saturated). The combined organic phases were dried over magnesium sulfate and concentrated to afford 2-iodo-1,3-dimethyl-5-(1,2,2,2-tetrafluoro-1-trifluoromethyl-ethyl)-benzene (61.3 g, 89% yield). $^1$H-NMR (CDCl$_3$, 400 MHz): 7.18 (s, 2H), 2.05 (s, 6H) ppm.

2-Iodo-1-methyl-5-(1,2,2,2-tetrafluoro-1-trifluoromethylethyl)-benzene was prepared from 4-heptafluoroisopropyl-2-methylaniline (prepared as described in EP 1,006,102) using the same procedure. The compound is also described in US 2003/187233.

2-Iodo-1,3-diethyl-5-(1,2,2,2-tetrafluoro-1-trifluoromethylethyl)-benzene was prepared from 4-heptafluoroisopropyl-2,6-diethylaniline (prepared as described in EP 1,006,102)

using the same procedure. ¹H-NMR (CDCl₃, 400 MHz): 7.24 (s, 2H), 2.86 (q, 4H), 1.22 (t, 6H) ppm.

Example I2

Preparation of 2,6-dimethyl-4-(1,2,2,2-tetrafluoro-1-trifluoromethyl-ethyl)-benzoic acid methyl ester

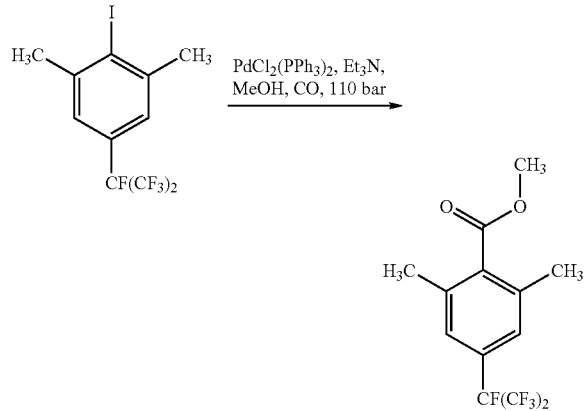

2-Iodo-1,3-dimethyl-5-(1,2,2,2-tetrafluoro-1-trifluoromethyl-ethyl)-benzene (30 g) (Example I1) was dissolved in methanol (300 ml) and triethylamine (22.5 ml). Then bis(triphenylphosphine)dichloropalladium(II) (5.64 g) was added. The mixture was reacted under a carbon monoxide atmosphere (110 bar) at 115° C. for 9 hours. The mixture was filtered to remove the solids and concentrated. The residue was purified by column chromatography on silica gel (eluent: cyclohexane/ethyl acetate 9:1) to afford 2,6-dimethyl-4-(1,2,2,2-tetra-fluoro-1-trifluoromethyl-ethyl)-benzoic acid methyl ester (15.5 g, 62% yield). ¹H-NMR (CDCl₃, 400 MHz): 7.37 (s, 2H), 3.93 (s, 3H), 2.37 (s, 6H) ppm.

2-Methyl-4-(1,2,2,2-tetrafluoro-1-trifluoromethyl-ethyl)-benzoic acid methyl ester was prepared from 2-iodo-1-methyl-5-(1,2,2,2-tetrafluoro-1-trifluoromethylethyl)-benzene (Example I1) using the same procedure. The compound is also described in US 2003/187233.

2,6-Diethyl-4-(1,2,2,2-tetrafluoro-1-trifluoromethyl-ethyl)-benzoic acid methyl ester was prepared from 2-iodo-1,3-diethyl-5-(1,2,2,2-tetrafluoro-1-trifluoromethylethyl)-benzene (Example I1) using the same procedure. ¹H-NMR (CDCl₃, 400 MHz): 7.31 (s, 2H), 3.94 (s, 3H), 2.65 (q, 4H), 1.23 (t, 6H) ppm.

Example I3

Preparation of 2,6-dimethyl-4-(1,2,2,2-tetrafluoro-1-trifluoromethyl-ethyl)-benzoic acid

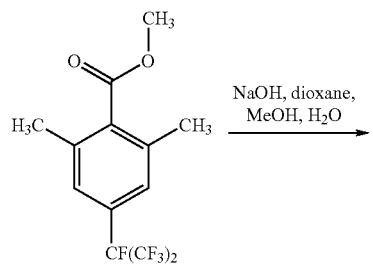

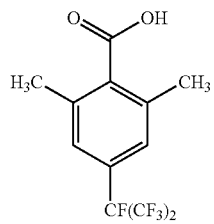

2,6-Dimethyl-4-(1,2,2,2-tetrafluoro-1-trifluoromethyl-ethyl)-benzoic acid methyl ester (7 g, 0.021 mol) (Example I2) was dissolved in dioxane (70 ml) and methanol (15 ml), then aqueous sodium hydroxide (4N) (52.2 ml, 0.21 mol) was added. The mixture was stirred at 60° C. for 15 hours. The methanol was evaporated and the mixture was cooled to 0° C. before acidifying to pH=1 by addition of concentrated hydrochloric acid. The mixture was extracted three times with ethyl acetate. The combined organic phases were washed with water, dried over sodium sulfate and concentrated to give the 2,6-dimethyl-4-(1,2,2,2-tetra-fluoro-1-trifluoromethyl-ethyl)-benzoic acid (6.52 g, 98% yield). ¹H-NMR (CDCl₃, 400 MHz): 7.31 (s, 2H), 2.49 (s, 6H) ppm.

2-Methyl-4-(1,2,2,2-tetrafluoro-1-trifluoromethyl-ethyl)-benzoic acid was prepared from 2-methyl-4-(1,2,2,2-tetrafluoro-1-trifluoromethyl-ethyl)-benzoic acid methyl ester (Example I2) using the same procedure. The compound is also described in US 2003/187233.

2,6-Diethyl-4-(1,2,2,2-tetrafluoro-1-trifluoromethyl-ethyl)-benzoic acid was prepared from 2,6-diethyl-4-(1,2,2,2-tetrafluoro-1-trifluoromethyl-ethyl)-benzoic acid methyl ester (Example I2) using the same procedure. ¹H-NMR (CDCl₃, 400 MHz): 7.38 (s, 2H), 2.79 (q, 4H), 1.30 (t, 6H) ppm.

Example I4

Preparation of 2,6-dimethyl-4-(1,2,2,2-tetrafluoro-1-trifluoromethyl-ethyl)-benzoyl chloride

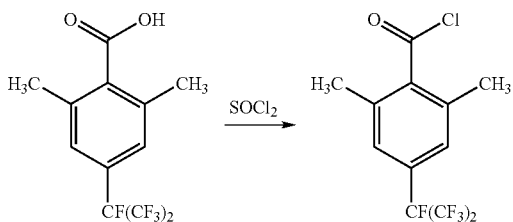

A suspension of 2,6-dimethyl-4-(1,2,2,2-tetrafluoro-1-trifluoromethyl-ethyl)-benzoic acid (100 mg, 0.31 mmol) (Example I3) in thionyl chloride (3 ml) was stirred at 85° C. under an atmosphere of nitrogen for 16 hours. The reaction mixture was cooled and concentrated. The residue was suspended in diethyl ether and the solvent was evaporated. The compound was used without further purification.

2-Methyl-4-(1,2,2,2-tetrafluoro-1-trifluoromethyl-ethyl)-benzoyl chloride was prepared from 2-methyl-4-(1,2,2,2-tetrafluoro-1-trifluoromethyl-ethyl)-benzoic acid (Example I3) using the same procedure. The compound was used without further purification.

2,6-Diethyl-4-(1,2,2,2-tetrafluoro-1-trifluoromethyl-ethyl)-benzoyl chloride was prepared from 2,6-diethyl-4-(1, 2,2,2-tetrafluoro-1-trifluoromethyl-ethyl)-benzoic acid (Example I3) using the same procedure. The compound was used without further purification.

Example I5

Preparation of 4-fluoro-N-(3-nitro-phenyl)-benzamide

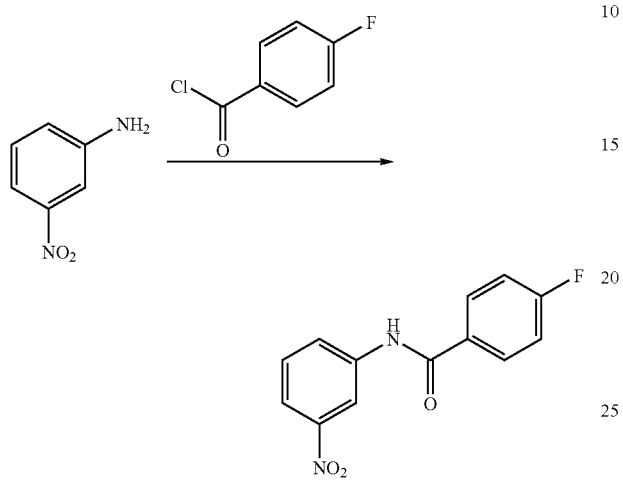

3-Nitro-phenylamine (5 g, 36.2 mmol) was dissolved in a biphasic mixture of ethyl acetate (100 ml) and aqueous sodium hydrogen carbonate (1N) (100 ml). 4-Fluoro-benzoyl-chloride (8.7 ml, 41.6 mmol) was added under vigorous stirring. The mixture was stirred for 2 hours at ambient temperature. The phases were separated, the organic phase was dried over sodium sulfate and concentrated. The residue was used without further purification (9.4 g, 100% yield). $^1$H-NMR (CDCl$_3$, 400 MHz) as disclosed in Magnetic Resonance in Chemistry (1997), 35(8), 543-548.

Example I6

Preparation of N-(3-amino-phenyl)-4-fluoro-benzamide

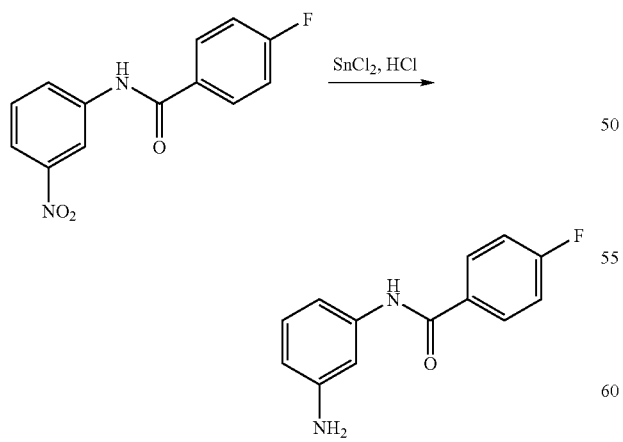

4-Fluoro-N-(3-nitro-phenyl)-benzamide (10.0 g, 36.2 mmol) (Example I5) was dissolved in isopropanol (150 ml) and tin chloride (24.7 g, 130.3 mmol) was added. The mixture was cooled to 0° C. and a solution of concentrated hydrochloric acid (20 ml) was added slowly. The reaction mixture was stirred at 80° C. for 2 hours. Then ⅓ of the total volume of isopropanol was evaporated. Water (200 ml) was added to the concentrated mixture and a solution of aqueous sodium hydroxide (4N) was added to adjust the pH to 7-8. The phases were separated and the aqueous phase was extracted three times with ethyl acetate (200 ml). The combined organic extracts were dried over sodium sulfate and concentrated. The residue was purified by column chromatography on silica gel (eluent: ethyl acetate) to give N-(3-amino-phenyl)-4-fluoro-benzamide (5 g, 60% yield). $^1$H-NMR (CDCl$_3$, 400 MHz): 7.93 (m, 2H), 7.27 (t, 2H), 7.01 (m, 1H), 6.89 (t, 1H), 6.78 (d, 1H), 5.01 (s, 2H) ppm.

Example P1

Preparation of N-[3-(4-fluoro-benzoylamino)-phenyl]-2,6-dimethyl-4-(1,2,2,2-tetrafluoro-1-trifluoromethyl-ethyl)-benzamide

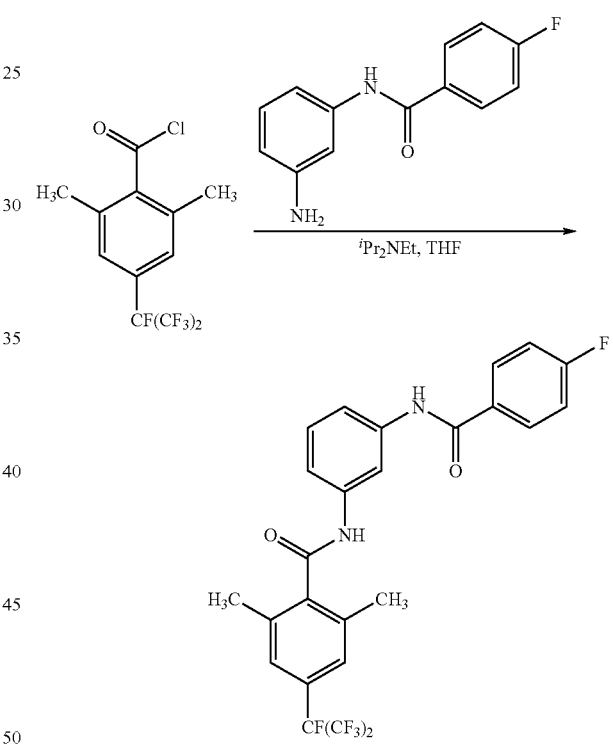

To a mixture of N-(3-amino-phenyl)-4-fluoro-benzamide (73 mg, 0.31 mmol) (Example I6) and Hunig's base (0.11 ml, 0.63 mmol) in anhydrous tetrahydrofuran (3 ml) under an atmosphere of nitrogen was added 2,6-dimethyl-4-(1,2,2,2-tetrafluoro-1-trifluoro-methyl-ethyl)-benzoyl chloride (0.31 mmol) (Example I4) dissolved in anhydrous tetrahydro-furan (2 ml). The reaction mixture was stirred at ambient temperature for 16 hours. Then the reaction mixture was diluted with ethyl acetate. The phases were separated and the organic phase was washed twice with aqueous sodium hydrogen carbonate (saturated). The combined organic phases were dried over sodium sulfate and concentrated. The residue was purified by column chromatography on silica gel (eluent: hexane/ethyl acetate 1:1) to give Compound A1 of Table A as a brownish residue (53.4 mg, 32% yield). $^1$H-NMR (MeOD, 400 MHz): 8.16 (t, 1H), 8.02-7.97 (m, 2H), 7.50-7.36 (m, 5H), 7.26-7.21 (m, 2H), 2.46 (s, 6H) ppm.

Example I7

Preparation of N-(3-amino-phenyl)-2,6-dimethyl-4-(1,2,2,2-tetrafluoro-1-trifluoromethyl-ethyl)-benzamide

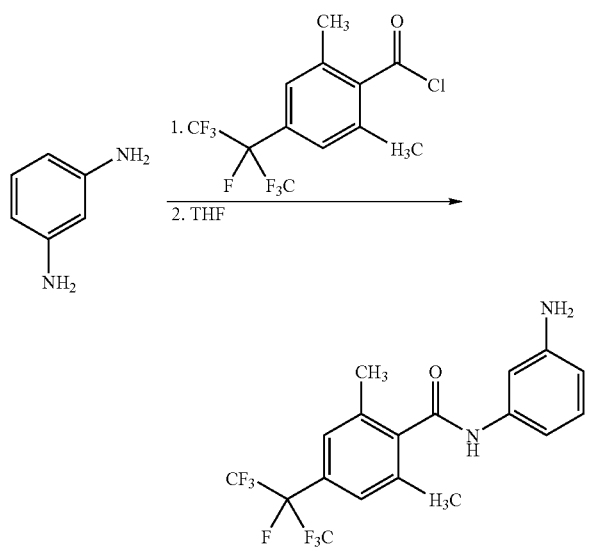

To a solution of benzene-1,3-diamine (4.48 g, 41.4 mmol) in anhydrous tetrahydrofuran (3 ml) under an atmosphere of nitrogen was added 2,6-dimethyl-4-(1,2,2,2-tetrafluoro-1-trifluoromethyl-ethyl)-benzoyl chloride (4.40 g, 13.8 mmol) (Example I4) dissolved in anhydrous tetrahydrofuran (3 ml). The reaction mixture was stirred at 70° C. for 48 hours. Then the reaction mixture was diluted with ethyl acetate and aqueous sodium hydrogen carbonate (saturated). The phases were separated and the aqueous phase was extracted twice with ethyl acetate. The combined organic phases were dried over sodium sulfate and concentrated. The residue was purified by column chromatography on silica gel (eluent: cyclohexane/ethyl acetate 3:1) to give N-(3-amino-phenyl)-2,6-dimethyl-4-(1,2,2,2-tetrafluoro-1-trifluoromethyl-ethyl)-benzamide (3.4 mg, 61% yield). $^1$H-NMR (CDCl$_3$, 400 MHz): 7.34 (t, 1H), 7.30 (s, 2H), 7.15 (t, 1H), 6.75 (d, 2H), 6.52 (d, 2H), 2.46 (s, 6H) ppm.

N-(3-Amino-phenyl)-2-methyl-4-(1,2,2,2-tetrafluoro-1-trifluoromethyl-ethyl)-benzamide was prepared from benzene-1,3-diamine and 2-methyl-4-(1,2,2,2-tetrafluoro-1-trifluoromethyl-ethyl)-benzoyl chloride (Example I4) using the same procedure. $^1$H-NMR (CDCl$_3$, 400 MHz): 7.6 (m, 1H), 7.52 (s, 2H), 7.40 (s, 1H), 7.30 (s, 1H), 7.13 (t, 1H), 6.72 (d, 1H), 6.50 (d, 1H), 3.76 (s, 2H), 2.24 (s, 3H) ppm.

N-(3-Amino-phenyl)-2,6-diethyl-4-(1,2,2,2-tetrafluoro-1-trifluoromethyl-ethyl)-benzamide was prepared from benzene-1,3-diamine and 2,6-diethyl-4-(1,2,2,2-tetrafluoro-1-trifluoromethyl-ethyl)-benzoyl chloride (Example I4) using the same procedure. $^1$H-NMR (CDCl$_3$, 400 MHz): 7.4 (m, 3H), 7.22 (s, 1H), 7.15 (t, 1H), 6.72 (dd, 1H), 6.52 (dd, 1H), 2.80 (q, 4H), 1.30 (t, 6H) ppm.

Example P2

Preparation of N-[3-(4-cyano-benzoylamino)-phenyl]-2,6-dimethyl-4-(1,2,2,2-tetrafluoro-1-trifluoromethyl-ethyl)-benzamide

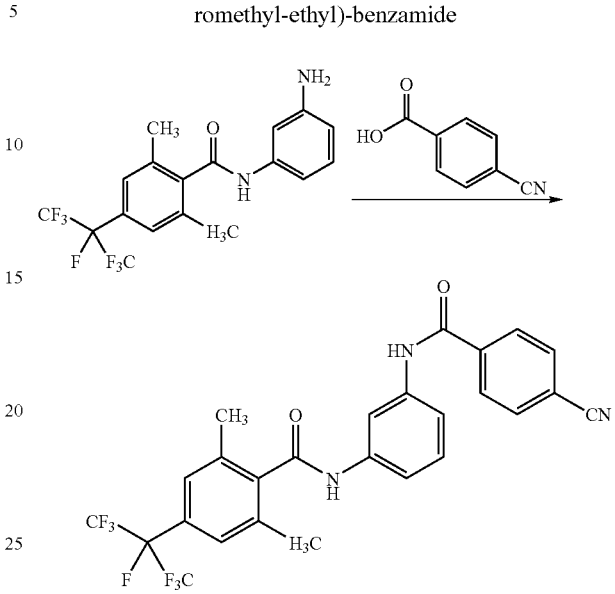

First Alternative:

This method was used to prepare a number of compounds (Compound A3 of Table A, Compound A23 to Compound A28 of Table A, Compound A30 to Compound 32 of Table A, Compound A88 to Compound A92 of Table A, and Compound A93 to Compound A94 of Table A). The method below describes the synthesis of Compound A3 of Table A. The other compounds were made by analogous methods.

N-(3-amino-phenyl)-2,6-dimethyl-4-(1,2,2,2-tetrafluoro-1-trifluoromethyl-ethyl)-benzamide (200 mg, 0.49 mmol) (Example I7) was dissolved in a biphasic mixture of ethyl acetate (4 ml) and aqueous sodium bicarbonate (1N) (4 ml). 4-Cyano-benzoyl chloride (166 mg, 1 mmol) was added under vigorous stirring. The reaction mixture was stirred for 3 hours at ambient temperature. The phases were separated, the organic phase was dried over sodium sulfate and concentrated. Purification: the residue was dissolved in ethyl acetate and precipitated with cyclohexane to gave Compound No. A3 of Table A below (200 mg, 77% yield). M.p. 213-216° C.

Second Alternative:

This method was used to prepare a number of compounds (Compound A1 to Compound A22 of Table A, Compound A29 of Table A, Compound A33 to Compound A86 of Table A, Compound A92 of Table A, and Compound A95 to Compound A112 of Table A) in parallel. The method below describes the synthesis of Compound A3 of Table A. The other compounds were made by analogous methods.

Stock solution A and solution C were used in all of these reactions, stock solutions B1 to B22, B29, B33 to B86, B92, and B95 to B112 were used only once in the synthesis of the corresponding compound, respectively. Stock solutions B1 to B22, B29, B33 to B86, B92, and B95 to B112 were each prepared using 1 mol of the acid in dimethyl acetamide (10 ml). Stock solution A was prepared by dissolving N-(3-amino-phenyl)-2,6-dimethyl-4-(1,2,2,2-tetrafluoro-1-trifluoromethyl-ethyl)-benzamide (1 mol) (Example I7) in dimethyl acetamide (10 ml). Stock solution C was prepated by dissolving BOP-Cl (bis(2-oxo-3-oxazolidinyl)phosphonic chloride (1.13 mmol) in dimethyl acetamide (9 ml).

Stock solution A (0.2 ml) was added into a well, followed by successive addition of stock solution B (0.35 ml), stock solution C (0.3 ml) and diisopropylethylamine (Hunig's Base) (50 μl). The mixture was stirred at room temperature for 20 minutes, then heated to 80° C. for 2 hours. The solution was stirred at room temperature for 24 hours. The mixture was purified by HPLC to give Compound A3 of Table A.

Example I8

Preparation of N-(5-nitro-2-cyano-phenyl)-4-fluoro-benzamide

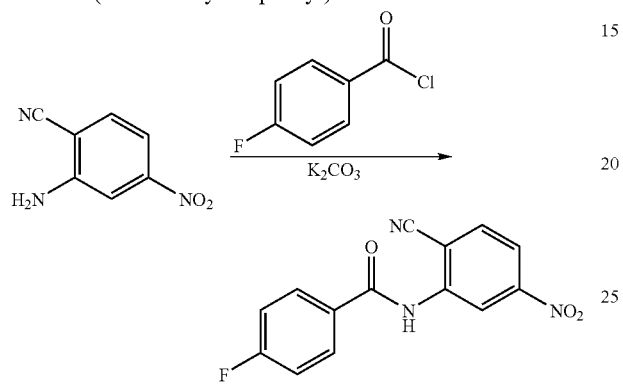

To a mixture of 2-amino-4-nitro-benzonitrile (3.3 g, 20.23 mmol) and pyridine (4.88 ml, 60.68 mmol) in anhydrous tetrahydrofuran (30 ml) under an atmosphere of nitrogen was added 4-fluorobenzoyl chloride (2.67 ml, 22.25 mmol). The reaction mixture was stirred at ambient temperature for 1 hour. Then more 4-fluorobenzoyl chloride (2.67 ml, 22.25 mmol) was added to the mixture. The reaction mixture was stirred at 50° C. for 1 hour. The reaction mixture was diluted with ethyl acetate and aqueous sodium hydrogen carbonate (saturated). The phases were separated and the aqueous phase was extracted twice with ethyl acetate. The combined organic phases were dried over sodium sulfate and concentrated. The residue was dissolved in methanol (200 ml) and potassium carbonate (5.1 g) was added. The reaction mixture was stirred for 16 hours at ambient temperature. The reaction mixture was diluted with ethyl acetate and aqueous sodium hydrogen carbonate (saturated). The phases were separated and the aqueous phase was extracted twice with ethyl acetate. The combined organic phases were dried over sodium sulfate and concentrated. The residue was purified by column chromatography on silica gel (eluent: cyclohexane/tetrahydrofuran 10:1) to give N-(2-cyano-5-nitro-phenyl)-4-fluoro-benzamide (1.82 g, 32% yield). $^1$H-NMR (DMSO-$d_6$, 400 MHz): 11.02 (s, 1H), 8.48 (s, 1H), 8.20 (s, 2H), 8.11 (m, 2H), 7.45 (m, 2H) ppm.

Example I9

Preparation of N-(5-amino-2-cyano-phenyl)-4-fluoro-benzamide

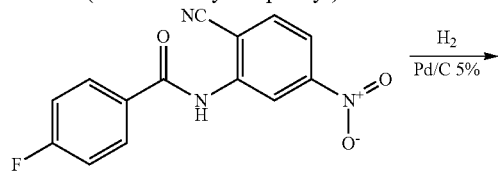

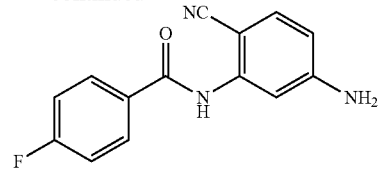

To a solution of N-(5-nitro-2-cyano-phenyl)-4-fluoro-benzamide (1.79 g) (Example 18) in a mixture of toluene (100 ml) and water (10 ml) was added palladium on charcoal (5%) (180 mg). The reactor was charged with hydrogen (471.72 ml, 10 bar) and the reaction mixture was heated to 80° C. for 4 hours. The reaction mixture was filtered to remove the palladium catalyst and the filtrate concentrated. The residue was purified by column chromatography on silica gel (eluent: cyclohexane/tetrahydrofuran 1:1) to give N-(5-amino-2-cyano-phenyl)-4-fluoro-benzamide (1.2 g, 75% yield). $^1$H-NMR (CDCl$_3$, 400 MHz): 8.28 (s, 1H), 7.98 (m, 3H), 7.40 (d, 1H), 7.22 (t, 1H), 6.43 (m, 1H), 4.3 (s, 2H) ppm.

Example P3

Preparation of N-[4-cyano-3-(4-fluoro-benzoylamino)-phenyl]-2,6-dimethyl-4-(1,2,2,2-tetrafluoro-1-trifluoromethyl-ethyl)-benzamide

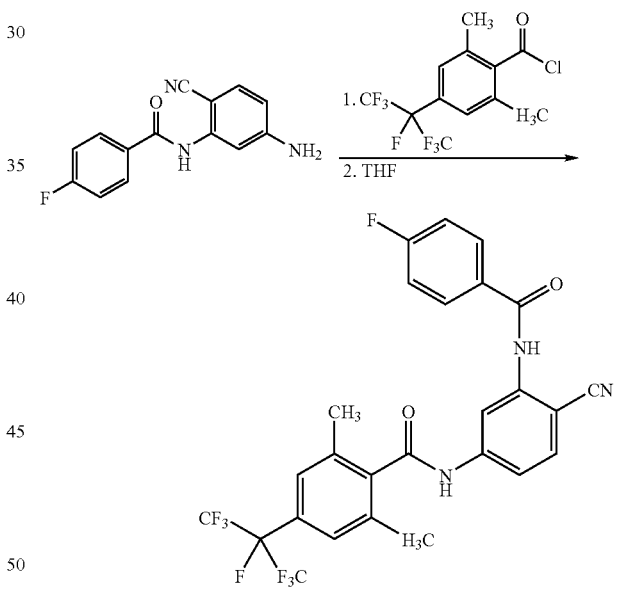

To a solution of N-(5-amino-2-cyano-phenyl)-4-fluoro-benzamide (0.20 g, 0.78 mmol) (Example I9) in anhydrous tetrahydrofuran (2.5 ml) under an atmosphere of nitrogen was added at room temperature a solution of 2,6-dimethyl-4-(1,2,2,2-tetrafluoro-1-trifluoromethyl-ethyl)-benzoyl chloride (0.332 g, 1.04 mmol) (Example I4) in anhydrous tetrahydrofuran (2.5 ml). The reaction mixture was stirred at room temperature for 48 hours. The reaction mixture was diluted with ethyl acetate and aqueous sodium hydrogen carbonate (saturated). The phases were separated and the aqueous phase was extracted twice with ethyl acetate. The combined organic phases were dried over sodium sulfate and concentrated. The residue was purified by column chromatography on silica gel (eluent: cyclohexane/ethyl acetate 3:1) to give N-[4-cyano-3-(4-fluoro-benzoylamino)-phenyl]-2,6-dimethyl-4-(1,2,2,2- tetrafluoro-1-trifluoromethyl-ethyl)-benzamide (131 mg, 66% yield). $^1$H-NMR (CDCl$_3$, 400 MHz): 8.98 (s, 1H), 8.51 (d, 1H), 8.45 (s, 1H), 8.33 (s, 1H), 8.21 (dd, 1H), 7.84 (m, 2H), 7.68 (d, 1H), 7.34 (s, 1H), 6.78 (t, 2H) ppm.

The following methods were used for HPLC-MS analysis:
Method A: Method (Water Alliance 2795 LC) with the following HPLC gradient conditions (Solvent A: 0.1% of formic acid in water/acetonitrile (9:1) and Solvent B: 0.1% of formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.
Method B: ZQ Mass Spectrometer from Waters (Single quadropole mass spectrometer)
Ionisation method: Electrospray, polarity: positive ions, capillary (kV) 3.00, cone (V) 30.00, extractor (V) 2.00, source temperature (° C.) 100, desolvation temperature (° C.) 250, cone gas flow (L/Hr) 50, desolvation gas flow (L/Hr) 400, mass range: 150 to 1000 Da, DAD wavelength range (nm): 200 to 500.
HPLC is from Agilent: quarternary HPLC pump HP1100, HP1100 diode array detector, HP1100 thermostat column compartment and HP1100 sovent degasser.
Gradient conditions (Solvent A: water with 0.04% of formic acid; Solvent B: acetonitrile/methanol (4:1, v/v) with 0.05% of formic acid)

| Time (minutes) | A (%) | B (%) | C (%) | D (%) | Flow rate (ml/min) |
|---|---|---|---|---|---|
| 0 | 95 | 5 | 0 | 0 | 1.7 |
| 2.0 | 0 | 100 | 0 | 0 | 1.7 |
| 2.8 | 0 | 100 | 0 | 0 | 1.7 |
| 2.9 | 95 | 5 | 0 | 0 | 1.7 |
| 3.1 | 95 | 5 | 0 | 0 | 1.7 |

Type of column: Phenomenex Gemini C18; Column length: 30 mm; Internal diameter of column: 3 mm; Particle Size: 3 micron; Temperature: 60° C.

The characteristic values obtained for each compound were the retention time ("RT", recorded in minutes) and the molecular ion, typically the cation MH$^+$, as listed in Tables A, B and C.

Table A: Compounds of Formula (Ia):

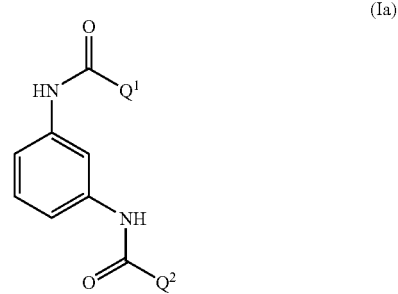

(Ia)

| Compound No. | Q$^1$ | Q$^2$ | M.p. (° C.) | RT min (method) | MH$^+$ |
|---|---|---|---|---|---|
| A1 | 4-fluoro-phenyl- | 2,6-dimethyl-4-perfluoroisopropyl-phenyl- | — | 2.08 (A) | 531.1 |
| A2 | 2-fluoro-pyrid-3-yl- | 2,6-dimethyl-4-perfluoroisopropyl-phenyl- | — | 1.9 (A) | 532.1 |
| A3 | 4-cyano-phenyl- | 2,6-dimethyl-4-perfluoroisopropyl-phenyl- | — | 2.0 (A) | 538.1 |
| A4 | 3-chloro-phenyl- | 2,6-dimethyl-4-perfluoroisopropyl-phenyl- | — | 2.2 (A) | 547.1 |
| A5 | 2-chloro-phenyl- | 2,6-dimethyl-4-perfluoroisopropyl-phenyl- | — | 2.07 (A) | 547.1 |
| A6 | 2-chloro-pyrid-4-yl- | 2,6-dimethyl-4-perfluoroisopropyl-phenyl- | — | 2.03 (A) | 548.1 |
| A7 | 5-bromo-pyrid-3-yl- | 2,6-dimethyl-4-perfluoroisopropyl-phenyl- | — | 2.03 (A) | 592 |
| A8 | 5-bromo-furan-2-yl- | 2,6-dimethyl-4-perfluoroisopropyl-phenyl- | — | 2.11 (A) | 581 |
| A9 | 2-bromo-phenyl- | 2,6-dimethyl-4-perfluoroisopropyl-phenyl- | — | 2.1 (A) | 591 |
| A10 | 3-chloro-5-trifluoromethyl-pyrid-2-yl- | 2,6-dimethyl-4-perfluoroisopropyl-phenyl- | — | 2.23 (A) | 616.1 |
| A11 | 2-methylthio-pyrid-3-yl- | 2,6-dimethyl-4-perfluoroisopropyl-phenyl- | — | 2.01 (A) | 560.1 |
| A12 | 2-fluoro-3-trifluoromethyl-phenyl- | 2,6-dimethyl-4-perfluoroisopropyl-phenyl- | — | 2.2 (A) | 599.1 |
| A13 | 2,5-dichloro-phenyl- | 2,6-dimethyl-4-perfluoroisopropyl-phenyl- | — | 2.2 (A) | 581.1 |
| A14 | 6-chloro-pyrid-3-yl- | 2,6-dimethyl-4-perfluoroisopropyl-phenyl- | — | 2.01 (A) | 548.1 |
| A15 | 4-nitro-phenyl- | 2,6-dimethyl-4-perfluoroisopropyl-phenyl- | — | 2.09 (A) | 558.1 |
| A16 | Phenyl- | 2,6-dimethyl-4-perfluoroisopropyl-phenyl- | — | 2.0 (A) | 531.1 |

-continued

| Compound No. | Q¹ | Q² | M.p. (° C.) | RT min (method) | MH⁺ |
|---|---|---|---|---|---|
| A17 | 2,3-difluoro-phenyl- | 2,6-dimethyl-4-per-fluoroisopropyl-phenyl- | — | 2.1 (A) | 549.1 |
| A18 | 5-chloro-thiophen-2-yl- | 2,6-dimethyl-4-per-fluoroisopropyl-phenyl- | — | 2.22 (A) | 553.1 |
| A19 | 2,5-dimethyl-2H-pyrazol-3-yl- | 2,6-dimethyl-4-per-fluoroisopropyl-phenyl- | — | 1.92 (A) | 531.2 |
| A20 | 1,2,3-thiadiazol-4-yl- | 2,6-dimethyl-4-per-fluoroisopropyl-phenyl- | — | 1.9 (A) | 521.1 |
| A21 | 3-methyl-pyrid-2-yl- | 2,6-dimethyl-4-per-fluoroisopropyl-phenyl- | — | 2.16 (A) | 528.1 |
| A22 | 2-methyl-phenyl- | 2,6-dimethyl-4-per-fluoroisopropyl-phenyl- | — | 2.1 (A) | 527.1 |
| A23 | 2-(3'-chloro-pyrid-2'-yl)-5-trifluoromethyl-2H-pyrazol-3-yl- | 2-methyl-4-per-fluoroisopropyl-phenyl- | 167-171 | — | — |
| A24 | phenyl- | 2-methyl-4-per-fluoroisopropyl-phenyl- | 135-139 | — | — |
| A25 | pyrid-3-yl- | 2-methyl-4-per-fluoroisopropyl-phenyl- | 143-146 | — | — |
| A26 | 4-nitro-phenyl- | 2-methyl-4-per-fluoroisopropyl-phenyl- | 120-130 | — | — |
| A27 | 2-chloro-pyrid-3-yl- | 2,6-dimethyl-4-per-fluoroisopropyl-phenyl- | 162-166 | — | — |
| A28 | 4-(N',N'-dimethyl-amino)-phenyl- | 2,6-dimethyl-4-per-fluoroisopropyl-phenyl- | 243-247 | — | — |
| A29 | 4-methoxy-carbonyl-phenyl- | 2,6-dimethyl-4-per-fluoroisopropyl-phenyl- | — | 2.01 (A) | 543.1 |
| A30 | 4-amino-phenyl- | 2,6-dimethyl-4-per-fluoroisopropyl-phenyl- | 268-272 | — | — |
| A31 | 1-methyl-3-trifluoromethyl-1H-pyrrol-4-yl- | 2,6-dimethyl-4-per-fluoroisopropyl-phenyl- | 196-199 | — | — |
| A32 | 1-methyl-3-trifluoromethyl-1H-pyrazol-4-yl- | 2,6-dimethyl-4-per-fluoroisopropyl-phenyl- | 186-189 | — | — |
| A33 | 2-fluoro-phenyl- | 2,6-dimethyl-4-per-fluoroisopropyl-phenyl- | — | 2.08 (A) | 531 |
| A34 | 2-methylthio-4-trifluoromethyl-phenyl- | 2,6-dimethyl-4-per-fluoroisopropyl-phenyl- | — | 2.2 (A) | 627.1 |
| A35 | furan-2-yl- | 2,6-dimethyl-4-per-fluoroisopropyl-phenyl- | — | 1.86 (A) | 503.1 |
| A36 | 4-trifluoro-methoxy-phenyl- | 2,6-dimethyl-4-per-fluoroisopropyl-phenyl- | — | 2.2 (A) | 597.1 |
| A37 | 4-fluoro-3-trifluoromethyl-phenyl- | 2,6-dimethyl-4-per-fluoroisopropyl-phenyl- | — | 2.2 (A) | 599.1 |
| A38 | 4-trifluoro-methyl-phenyl- | 2,6-dimethyl-4-per-fluoroisopropyl-phenyl- | — | 2.2 (A) | 581.1 |
| A39 | 2-methoxy-phenyl- | 2,6-dimethyl-4-per-fluoroisopropyl-phenyl- | — | 2.1 (A) | 543.1 |
| A40 | 2-trifluoro-methyl-phenyl- | 2,6-dimethyl-4-per-fluoroisopropyl-phenyl- | — | 2.04 (A) | 581.1 |
| A41 | pyrid-4-yl- | 2,6-dimethyl-4-per-fluoroisopropyl-phenyl- | — | 1.7 (A) | 514.1 |
| A42 | 4-methyl-1,2,3-thiadiazol-5-yl- | 2,6-dimethyl-4-per-fluoroisopropyl-phenyl- | — | 1.91 (A) | 535.1 |
| A43 | 2-fluoro-5-trifluoromethyl-phenyl- | 2,6-dimethyl-4-per-fluoroisopropyl-phenyl- | — | 2.2 (A) | 599.1 |
| A51 | 3-fluoro-4-hydroxy-phenyl- | 2,6-dimethyl-4-per-fluoroisopropyl-phenyl- | — | 2.0 (A) | 547.1 |
| A52 | benzo[1,2,5]thiadiazol-5-yl- | 2,6-dimethyl-4-per-fluoroisopropyl-phenyl- | — | 2.1 (A) | 571.1 |
| A53 | 4-(prop-2'-yl)-phenyl- | 2,6-dimethyl-4-per-fluoroisopropyl-phenyl- | — | 2.3 (A) | 555.2 |

-continued

| Compound No. | Q¹ | Q² | M.p. (° C.) | RT min (method) | MH⁺ |
|---|---|---|---|---|---|
| A54 | 4-methylthio-phenyl- | 2,6-dimethyl-4-per-fluoroisopropyl-phenyl- | — | 2.2 (A) | 559.1 |
| A55 | 2,3-dihydro-benzofuran-5-yl- | 2,6-dimethyl-4-per-fluoroisopropyl-phenyl- | — | 2.1 (A) | 555.1 |
| A56 | 5-bromo-2-hydroxy-phenyl- | 2,6-dimethyl-4-per-fluoroisopropyl-phenyl- | — | 2.3 (A) | 607.0 |
| A57 | 4-methoxy-phenyl- | 2,6-dimethyl-4-per-fluoroisopropyl-phenyl- | — | 2.1 (A) | 543.1 |
| A58 | 3-chloro-2,4,5-trifluoro-phenyl- | 2,6-dimethyl-4-per-fluoroisopropyl-phenyl- | — | 2.3 (A) | 601.1 |
| A59 | 4-(pyrrol-1'-yl)-phenyl- | 2,6-dimethyl-4-per-fluoroisopropyl-phenyl- | — | 2.2 (A) | 578.2 |
| A60 | 4-(1,2,3-thiadiazol-4'-yl)-phenyl- | 2,6-dimethyl-4-per-fluoroisopropyl-phenyl- | — | 2.13 (A) | 597.1 |
| A61 | 3,4-dihydro-2H-benzo[b][1,4]-dioxepin-7-yl- | 2,6-dimethyl-4-per-fluoroisopropyl-phenyl- | — | 2.13 (A) | 585.2 |
| A62 | 1H-benz-imidazol-5-yl- | 2,6-dimethyl-4-per-fluoroisopropyl-phenyl- | — | 1.57 (A) | 553.1 |
| A63 | biphenyl-4-yl- | 2,6-dimethyl-4-per-fluoroisopropyl-phenyl- | — | 2.3 (A) | 589.2 |
| A64 | 3-chloro-2-hydroxy-phenyl- | 2,6-dimethyl-4-per-fluoroisopropyl-phenyl- | — | 2.3 (A) | 563.1 |
| A67 | benzo[b]thio-phen-5-yl- | 2,6-dimethyl-4-per-fluoroisopropyl-phenyl- | — | 2.2 (A) | 569.1 |
| A69 | 1H-imidazol-4-yl- | 2,6-dimethyl-4-per-fluoroisopropyl-phenyl- | — | 1.66 (A) | 503.1 |
| A70 | quinoxalin-2-yl- | 2,6-dimethyl-4-per-fluoroisopropyl-phenyl- | — | 2.2 (A) | 565.1 |
| A71 | cinnolin-4-yl- | 2,6-dimethyl-4-per-fluoroisopropyl-phenyl- | — | 1.97 (A) | 565.1 |
| A72 | pyrid-3-yl- | 2,6-dimethyl-4-per-fluoroisopropyl-phenyl- | — | 1.84 (A) | 514.1 |
| A73 | 4-methoxy-thiophen-3-yl- | 2,6-dimethyl-4-per-fluoroisopropyl-phenyl- | — | 2.2 (A) | 549.1 |
| A74 | 5-phenyl-oxazol-4-yl- | 2,6-dimethyl-4-per-fluoroisopropyl-phenyl- | — | 2.3 (A) | 580.1 |
| A75 | 1,2,5-trimethyl-1H-pyrrol-3-yl- | 2,6-dimethyl-4-per-fluoroisopropyl-phenyl- | — | 2.1 (A) | 544.2 |
| A76 | 4-methyl-2-phenyl-pyrimid-5-yl | 2,6-dimethyl-4-per-fluoroisopropyl-phenyl- | — | 2.27 (A) | 605.2 |
| A77 | thiophen-2-yl- | 2,6-dimethyl-4-per-fluoroisopropyl-phenyl- | — | 2.08 (A) | 519.1 |
| A78 | 5-methyl-3-phenyl-isoxazol-4-yl- | 2,6-dimethyl-4-per-fluoroisopropyl-phenyl- | — | 2.18 (A) | 594.2 |
| A79 | quinolin-2-yl- | 2,6-dimethyl-4-per-fluoroisopropyl-phenyl- | — | 2.34 (A) | 564.1 |
| A81 | 4-methyl-2-phenyl-thiazol-5-yl- | 2,6-dimethyl-4-per-fluoroisopropyl-phenyl- | — | 2.3 (A) | 610.1 |
| A82 | 2,7-dimethyl-pyrazolo[1,5-a]-pyrimid-6-yl- | 2,6-dimethyl-4-per-fluoroisopropyl-phenyl- | — | 1.98 (A) | 582.2 |
| A83 | 4,5,6,7-tetra-hydro-benzo[c]-thiophen-1-yl- | 2,6-dimethyl-4-per-fluoroisopropyl-phenyl- | — | 2.3 (A) | 573.1 |
| A84 | 5-(pyrid-2'-yl)-thiophen-2-yl- | 2,6-dimethyl-4-per-fluoroisopropyl-phenyl- | — | 2.2 (A) | 596.1 |
| A85 | 5-phenyl-furan-2-yl- | 2,6-dimethyl-4-per-fluoroisopropyl-phenyl- | — | 2.3 (A) | 579.1 |
| A86 | 5-methyl-1-phenyl-1H-pyrazol-4-yl- | 2,6-dimethyl-4-per-fluoroisopropyl-phenyl- | — | 2.15 (A) | 593.2 |
| A88 | 3-fluoro-4-nitro-phenyl- | 2,6-dimethyl-4-per-fluoroisopropyl-phenyl- | 207-210 | — | — |
| A89 | 2-fluoro-4-nitro-phenyl- | 2,6-dimethyl-4-per-fluoroisopropyl-phenyl- | 176-179 | — | — |

-continued

| Compound No. | Q¹ | Q² | M.p. (° C.) | RT min (method) | MH⁺ |
|---|---|---|---|---|---|
| A90 | 3-fluoro-pyrid-4-yl- | 2,6-dimethyl-4-perfluoroisopropyl-phenyl- | 89-90 | — | — |
| A91 | 4-cyano-2-fluoro-phenyl- | 2,6-dimethyl-4-perfluoroisopropyl-phenyl- | 186-188 | — | — |
| A92 | 4-nitro-phenyl- | 2,6-diethyl-4-perfluoroisopropyl-phenyl- | — | 2.2 (A) | 586.1 |
| A93 | 5-bromo-furan-2-yl- | 2,6-diethyl-4-perfluoroisopropyl-phenyl- | 186-188 | — | — |
| A94 | 2,6-diethyl-4-perfluoro-isopropyl-phenyl- | 2,6-diethyl-4-perfluoroisopropyl-phenyl- | 182-190 | — | — |
| A95 | 2-fluoro-phenyl- | 2,6-diethyl-4-perfluoroisopropyl-phenyl- | — | 2.16 (A) | 559.2 |
| A96 | 2-methyl-phenyl- | 2,6-diethyl-4-perfluoroisopropyl-phenyl- | — | 2.17 (A) | 555.2 |
| A97 | 2-chloro-phenyl- | 2,6-diethyl-4-perfluoroisopropyl-phenyl- | — | 2.15 (A) | 575.1 |
| A98 | 2-methylthio-4-trifluoromethyl-phenyl- | 2,6-diethyl-4-perfluoroisopropyl-phenyl- | — | 2.3 (A) | 655.1 |
| A99 | 4-(N',N'-di-methylamino)-phenyl- | 2,6-diethyl-4-perfluoroisopropyl-phenyl- | — | 2.21 (A) | 584.2 |
| A100 | 5-chloro-2-fluoro-phenyl- | 2,6-diethyl-4-perfluoroisopropyl-phenyl- | — | 2.28 (A) | 593.1 |
| A101 | furan-2-yl- | 2,6-diethyl-4-perfluoroisopropyl-phenyl- | — | 2.03 (A) | 531.1 |
| A102 | 4-trifluoro-methoxy-phenyl- | 2,6-diethyl-4-perfluoroisopropyl-phenyl- | — | 2.3 (A) | 625.1 |
| A103 | 4-fluoro-3-trifluoromethyl-phenyl- | 2,6-diethyl-4-perfluoroisopropyl-phenyl- | — | 2.34 (A) | 627.1 |
| A104 | 4-trifluoro-methyl-phenyl- | 2,6-diethyl-4-perfluoroisopropyl-phenyl- | — | 2.31 (A) | 609.2 |
| A105 | 2-trifluoro-methoxy-phenyl- | 2,6-diethyl-4-perfluoroisopropyl-phenyl- | — | 2.24 (A) | 625.1 |
| A106 | 2-methoxy-phenyl- | 2,6-diethyl-4-perfluoroisopropyl-phenyl- | — | 2.24 (A) | 571.2 |
| A107 | phenyl- | 2,6-diethyl-4-perfluoroisopropyl-phenyl- | — | 2.15 (A) | 541.2 |
| A108 | 4-fluoro-phenyl- | 2,6-diethyl-4-perfluoroisopropyl-phenyl- | — | 2.19 (A) | 559.2 |
| A109 | 2-trifluoro-methyl-phenyl- | 2,6-diethyl-4-perfluoroisopropyl-phenyl- | — | 2.18 (A) | 609.2 |
| A110 | 2,3-difluoro-phenyl- | 2,6-diethyl-4-perfluoroisopropyl-phenyl- | — | 2.19 (A) | 577.1 |
| A111 | 4-methoxy-carbonyl-phenyl- | 2,6-diethyl-4-perfluoroisopropyl-phenyl- | — | 2.18 (A) | 599.2 |
| A112 | 2-fluoro-5-trifluoromethyl-phenyl- | 2,6-diethyl-4-perfluoroisopropyl-phenyl- | — | 2.3 (A) | 627.1 |

Table B: Compounds of Formula (Ib):

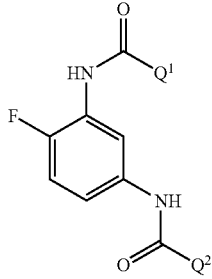

(Ib)

| Compound No. | $Q^1$ | $Q^2$ | M.p. (°C.) | RT min (method) | MH+ |
|---|---|---|---|---|---|
| B1 | 4-fluoro-phenyl- | 2,6-dimethyl-4-perfluoroisopropyl-phenyl- | — | 2.1 (A) | 549.1 |
| B2 | 2-chloro-pyrid-3-yl- | 2,6-dimethyl-4-perfluoroisopropyl-phenyl- | — | 2.01 (A) | 550.1 |
| B3 | 4-cyano-phenyl- | 2,6-dimethyl-4-perfluoroisopropyl-phenyl- | — | 2.0 (A) | 556.1 |
| B4 | 3-chloro-phenyl- | 2,6-dimethyl-4-perfluoroisopropyl-phenyl- | — | 2.2 (A) | 565.1 |
| B5 | 2-chloro-pyrid-4-yl- | 2,6-dimethyl-4-perfluoroisopropyl-phenyl- | — | 2.0 (A) | 566.1 |
| B6 | 5-bromo-pyrid-3-yl- | 2,6-dimethyl-4-perfluoroisopropyl-phenyl- | — | 2.0 (A) | 610.0 |
| B7 | 5-bromo-furan-2-yl- | 2,6-dimethyl-4-perfluoroisopropyl-phenyl- | — | 2.2 (A) | 599.0 |
| B8 | 2-bromo-phenyl- | 2,6-dimethyl-4-perfluoroisopropyl-phenyl- | — | 2.1 (A) | 609.0 |
| B9 | 2-methylthio-pyrid-3-yl- | 2,6-dimethyl-4-perfluoroisopropyl-phenyl- | — | 2.1 (A) | 578.1 |
| B10 | 2-fluoro-3-trifluoromethyl-phenyl- | 2,6-dimethyl-4-perfluoroisopropyl-phenyl- | — | 2.3 (A) | 617.1 |
| B11 | 2,5-dichloro-phenyl- | 2,6-dimethyl-4-perfluoroisopropyl-phenyl- | — | 2.2 (A) | 599.0 |
| B12 | 6-chloro-pyrid-3-yl- | 2,6-dimethyl-4-perfluoroisopropyl-phenyl- | — | 2.0 (A) | 566.1 |
| B13 | 4-nitro-phenyl- | 2,6-dimethyl-4-perfluoroisopropyl-phenyl- | — | 2.1 (A) | 576.1 |
| B14 | phenyl- | 2,6-dimethyl-4-perfluoroisopropyl-phenyl- | — | 2.1 (A) | 531.1 |
| B15 | 5-chloro-thiophen-2-yl- | 2,6-dimethyl-4-perfluoroisopropyl-phenyl- | — | 2.2 (A) | 571.0 |
| B16 | 2,5-dimethyl-2H-pyrazol-3-yl- | 2,6-dimethyl-4-perfluoroisopropyl-phenyl- | — | 2.0 (A) | 549.1 |
| B17 | 3-methyl-pyrid-2-yl- | 2,6-dimethyl-4-perfluoroisopropyl-phenyl- | — | 2.37 (A) | 546.1 |
| B18 | 2-methyl-phenyl- | 2,6-dimethyl-4-perfluoroisopropyl-phenyl- | — | 2.1 (A) | 545.1 |

Table C: Compounds of Formula (Ie):

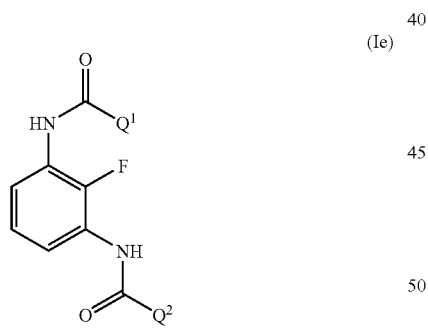

(Ie)

| Compound No. | $Q^1$ | $Q^2$ | M.p. (°C.) | RT min (method) | MH+ |
|---|---|---|---|---|---|
| C1 | 4-cyano-phenyl- | 2,6-dimethyl-4-perfluoroisopropyl-phenyl- | — | 2.07 (B) | 556.0 |
| C2 | phenyl- | 2,6-dimethyl-4-perfluoroisopropyl-phenyl- | — | 2.10 (B) | 531.0 |
| C3 | 4-fluoro-phenyl- | 2,6-dimethyl-4-perfluoroisopropyl-phenyl- | — | 2.12 (B) | 549.0 |
| C4 | 4-methyl-phenyl- | 2,6-dimethyl-4-perfluoroisopropyl-phenyl- | — | 2.16 (B) | 545.0 |
| C5 | 4-nitro-phenyl- | 2,6-dimethyl-4-perfluoroisopropyl-phenyl- | — | 2.11 (B) | 576.0 |

-continued

| Compound No. | $Q^1$ | $Q^2$ | M.p. (° C.) | RT min (method) | MH+ |
|---|---|---|---|---|---|
| C6 | 3-fluoro-phenyl- | 2,6-dimethyl-4-per-fluoroisopropyl-phenyl- | — | 2.12 (B) | 549.0 |
| C7 | 3-methyl-phenyl- | 2,6-dimethyl-4-per-fluoroisopropyl-phenyl- | — | 2.16 (B) | 545.0 |
| C8 | 3-nitro-phenyl- | 2,6-dimethyl-4-per-fluoroisopropyl-phenyl- | — | 2.11 (B) | 576.0 |
| C9 | 2-fluoro-phenyl- | 2,6-dimethyl-4-per-fluoroisopropyl-phenyl- | — | 2.15 (B) | 549.0 |
| C10 | 2-methyl-phenyl- | 2,6-dimethyl-4-per-fluoroisopropyl-phenyl- | — | 2.13 (B) | 545.0 |
| C11 | 2-nitro-phenyl- | 2,6-dimethyl-4-per-fluoroisopropyl-phenyl- | — | 2.05 (B) | 576.0 |

Table D: Compounds of Formula (If):

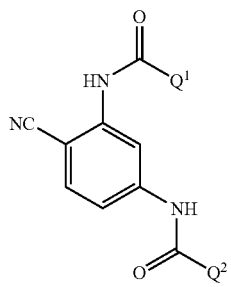

(If)

| Compound No. | $Q^1$ | $Q^2$ | M.p. (° C.) | RT min (method) | MH+ |
|---|---|---|---|---|---|
| D1 | 4-fluoro-phenyl- | 2,6-dimethyl-4-per-fluoroisopropyl-phenyl- | 81-83 | — | — |

Biological Examples

This Example illustrates the pesticidal/insecticidal properties of compounds of formula (I). Test against were performed as follows:

Spodoptera littoralis (Egyptian cotton leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behaviour, and growth regulation 3 days after treatment (DAT). The following compounds gave at least 80% control of Spodoptera littoralis: A1, A2, A3, A4, A5, A6, A7, A8, A9, A10, A11, A12, A13, A14, A15, A16, A17, A19, A20, A21, A22, A24, A27, A35, A36, A38, A41, A42, A45, A52, A55, A72, A75, A77, A90, A91, A92, A93, A96, A97, A100, A101, A106, A107, A110, B1, B2, B3, B5, B6, B7, B12, B14, B16, C1, C2, C3, C5, C6, C7, C8, C11, D1.

Heliothis virescens (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation. The following compounds gave at least 80% control of Heliothis virescens: A1, A2, A3, A4, A5, A6, A7, A8, A9, A10, A11, A12, A13, A14, A15, A16, A17, A18, A21, A22, A23, A27, A28, A30, A33, A37, A38, A55, A58, A72, A89, A91, A92, A93, A95, A96, A97, A100, A101, A103, A104, A107, A108, A109, A110, B1, B2, B3, B4, B5, B6, B7, B8, B12, B13, B14, B16, C1, C2, C3, C5, C6, C7, C8, C9, C11, D1.

Plutella xylostella (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 6 days, samples were checked for larval mortality and growth regulation. The following compounds gave at least 80% control of Plutella xylostella: A1, A2, A3, A4, A5, A6, A7, A8, A14, A15, A17, A26, A27, A89, A91, A92, A93, A95, B1, B3, B5, B6, B7, B13, B14, C1, C2, C3, C5, C6, C7, D1.

Diabrotica balteata (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation. The following compounds gave at least 80% control of Diabrotica balteata: A1, A2, A3, A5, A6, A7, A8, A10, A11, A14, A15, A17, A26, A27, A38, A89, A90, A91, A92, A93, A95, A97, A103, A108, B1, B3, B6, B7, B12, B14, C1, C3, C5, C6, D1.

Aedes aegypti (Yellow Fever Mosquito):

10-15 Aedes larvae (L2) together with a nutrition mixture are placed in 96-well microtiter plates. Test solutions at an application rate of 2 ppm were pipetted into the wells. 2 days later, insects were checked for mortality and growth inhibition. The following compounds gave at least 80% control of Aedes aegypti: A1, A2, A3, A6, A8, A14, A15, A16, A18, A23, A26, A27, B1.

The invention claimed is:
1. A compound of formula (I):

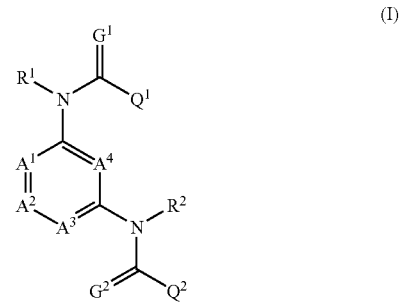

(I)

wherein
$A^1, A^2, A^3$ and $A^4$ are independently of one another C—X or nitrogen, provided that no more than two of $A^1, A^2, A^3$ and $A^4$ are nitrogen;
each X is independently hydrogen, halogen, cyano, $C_1$-$C_4$alkyl, $C_1$-$C_4$haloalkyl or $C_1$-$C_4$alkoxy;
$R^1$ and $R^2$ are independently of one another hydrogen, $C_1$-$C_4$alkyl or $C_1$-$C_4$alkylcarbonyl;
$G^1$ and $G^2$ are independently of one another oxygen or sulfur;
$Q^1$ is aryl or aryl substituted by one to five substituents $R^3$, which may be the same or different, or $Q^1$ is heterocyclyl or heterocyclyl substituted by one to five substituents $R^3$, which may be the same or different; wherein
each $R^3$ is independently cyano, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halo-cycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkyl-sulfinyl, $C_1$-$C_3$haloalkylsulfinyl, $C_1$-$C_3$alkylsulfonyl, $C_1$-$C_3$haloalkylsulfonyl, amino, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$alkylcarbonylamino, aryl which is optionally substituted by one to three substituents independently selected from halogen, $C_1$-$C_4$alkyl, $C_1$-$C_4$haloalkyl, $C_1$-$C_4$alkoxy or $C_1$-$C_4$haloalkoxy, or heteroaryl which is optionally substituted by one to three substituents independently selected from halogen, $C_1$-$C_4$alkyl, $C_1$-$C_4$haloalkyl, $C_1$-$C_4$alkoxy or $C_1$-$C_4$haloalkoxy; and
$Q^2$ is a moiety of formula (II) or (III)

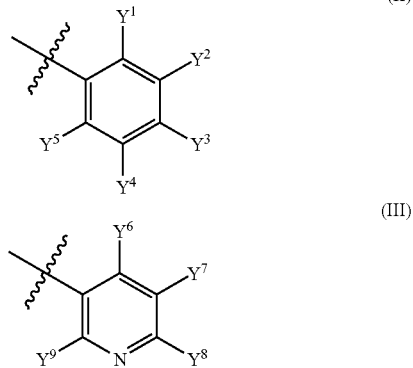

wherein
$Y^1$ and $Y^5$ are independently of each other hydrogen, cyano, halogen, $C_1$-$C_4$alkyl, $C_1$-$C_4$haloalkyl, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;
$Y^3$ is $C_2$-$C_6$ perfluoroalkyl, $C_1$-$C_6$perfluoroalkylthio, or $C_1$-$C_6$perfluoroalkylsulfinyl;
$Y^2$ and $Y^4$ are independently of each other hydrogen, halogen or $C_1$-$C_4$alkyl;
$Y^6$ and $Y^9$ are independently of each other hydrogen, cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$alkylsulfonyl or $C_1$-$C_3$haloalkylsulfonyl;

$Y^8$ is $C_1$-$C_4$haloalkoxy, $C_2$-$C_6$ perfluoroalkyl, $C_1$-$C_6$perfluoroalkylthio, $C_1$-$C_6$ perfluoroalkyl-sulfinyl or $C_1$-$C_6$perfluoroalkylsulfonyl;
$Y^7$ is hydrogen, halogen or $C_1$-$C_4$alkyl;
or salts or N-oxides thereof.

2. A compound according to claim 1 wherein $A^1$ is C—X.
3. A compound according to claim 1 wherein $A^2$ is C—X.
4. A compound according to claim 1 wherein $A^3$ is C—X.
5. A compound according to claim 1 wherein $A^4$ is C—X.
6. A compound according to claim 1 wherein each X is independently hydrogen, fluoro, chloro, bromo, cyano, methyl, trifluoromethyl or methoxy.
7. A compound according to claim 1 wherein $R^1$ is hydrogen, methyl, ethyl or acetyl.
8. A compound according to claim 1 wherein $R^2$ is hydrogen, methyl, ethyl or acetyl.
9. A compound according to claim 1 wherein $G^1$ is oxygen.
10. A compound according to claim 1 wherein $G^2$ is oxygen.
11. A compound according to claim 1 wherein $Q^1$ is phenyl, pyridyl, pyrimidyl, furanyl, thiophenyl, oxazolyl, isoxazolyl, thiazolyl, thiadiazolyl, pyrrolyl, pyrazolyl or imidazolyl, or phenyl, pyridyl, pyrimidyl, furanyl, thiophenyl, oxazolyl, isoxazolyl, thiazolyl, thiadiazolyl, pyrrolyl, pyrazolyl or imidazolyl substituted by one to four substituents independently selected from cyano, nitro, hydroxy, fluoro, chloro, bromo, methyl, trifluoromethyl, methoxy, methylthio, methylsulfinyl, methylsulfonyl or phenyl.
12. A compound according to claim 1 wherein $Q^2$ is a moiety of formula (II).
13. A compound according to claim 1 wherein $Q^2$ is 2,6-dimethyl-4-perfluoroisopropyl-phenyl.
14. A compound according to claim 1 wherein $Q^2$ is 2,6-diethyl-4-perfluoroisopropyl-phenyl.
15. A compound of formula (VIII')

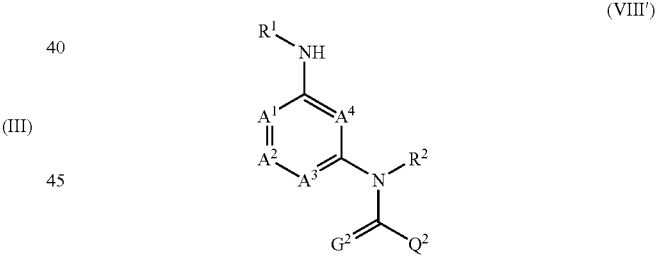

wherein
$A^1, A^2, A^3$ and $A^4$ are independently of one another C—X or nitrogen, provided that no more than two of $A^1, A^2, A^3$ and $A^4$ are nitrogen;
each X is independently hydrogen, halogen, cyano, $C_1$-$C_4$alkyl, $C_1$-$C_4$haloalkyl or $C_1$-$C_4$alkoxy;
$R^1$ and $R^2$ are independently of one another hydrogen, $C_1$-$C_4$alkyl or $C_1$-$C_4$alkylcarbonyl;
$G^1$ and $G^2$ are independently of one another oxygen or sulfur;
$Q^1$ is aryl or aryl substituted by one to five substituents $R^3$, which may be the same or different, or $Q^1$ is heterocyclyl or heterocyclyl substituted by one to five substituents $R^3$, which may be the same or different; wherein
each $R^3$ is independently cyano, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halo-cycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkyl-sulfinyl, $C_1$-$C_3$haloalkylsulfinyl, $C_1$-$C_3$alkylsulfonyl, $C_1$-$C_3$haloalkylsulfonyl, amino, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$alkylcarbonylamino, aryl which is optionally substituted by one to three substituents independently selected from halogen, $C_1$-$C_4$alkyl, $C_1$-$C_4$haloalkyl, $C_1$-$C_4$alkoxy or $C_1$-$C_4$haloalkoxy, or heteroaryl which is optionally substituted by one to three substituents independently selected from halogen, $C_1$-$C_4$alkyl, $C_1$-$C_4$haloalkyl, $C_1$-$C_4$alkoxyl or $C_1$-$C_4$haloalkoxy; and $Q^2$ is a moiety of formula (II) or (III)

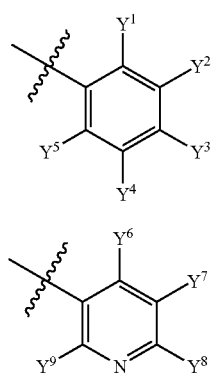

(II)

(III)

wherein $Y^1$ and $Y^5$ are independently of each other hydrogen, cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;

$Y^3$ is $C_2$-$C_6$perfluoroalkyl, $C_1$-$C_6$perfluoroalkylthio, or $C_1$-$C_6$perfluoroalkylsulfinyl;

$Y^2$ and $Y^4$ are independently of each other hydrogen, halogen or $C_1$-$C_4$alkyl;

$Y^6$ and $Y^9$ are independently of each other hydrogen, cyano, halogen, $C_1$-$C_4$alkyl, $C_1$-$C_4$halo-alkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_3$haloalkylsulfinyl, $C_1$-$C_3$alkylsulfonyl or $C_1$-$C_3$haloalkylsulfonyl;

$Y^8$ is $C_1$-$C_4$haloalkoxy, $C_2$-$C_6$perfluoroalkyl, $C_1$-$C_6$perfluoroalkylthio, $C_1$-$C_6$perfluoroalkyl-sulfinyl or $C_1$-$C_6$ perfluoroalkylsulfonyl;

$Y^7$ is hydrogen, halogen or $C_1$-$C_4$alkyl;

or salts or N-oxides thereof.

16. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

17. An insecticidal, acaricidal, nematicidal or molluscicidal composition comprising an insecticidally, acaricidally, nematicidally or molluscicidally effective amount of a compound of formula (I) as defined in claim 1.

* * * * *